US008227186B1

(12) United States Patent
Miller et al.

(10) Patent No.: US 8,227,186 B1
(45) Date of Patent: Jul. 24, 2012

(54) METHODS AND COMPOSITIONS RELATING TO BIOLUMINESCENT MICROORGANISMS

(75) Inventors: Sally Ann Miller, Wooster, OH (US); Gireesh Rajashekara, Wooster, OH (US); Xiulan Xu, Wooster, OH (US)

(73) Assignee: The Ohio State University Research Foundation, Columbus, OH (US)

( * ) Notice: Subject to any disclaimer, the term of this patent is extended or adjusted under 35 U.S.C. 154(b) by 94 days.

(21) Appl. No.: 12/510,023

(22) Filed: Jul. 27, 2009

Related U.S. Application Data

(60) Provisional application No. 61/083,783, filed on Jul. 25, 2008.

(51) Int. Cl.
*C12Q 1/68* (2006.01)

(52) U.S. Cl. .......... 435/6; 435/7.1; 435/252; 435/320.1; 435/69.1

(58) Field of Classification Search ........................ None
See application file for complete search history.

(56) References Cited

U.S. PATENT DOCUMENTS

| | | | |
|---|---|---|---|
| 6,110,661 | A | 8/2000 | Lajoie et al. |
| 6,258,604 | B1 | 7/2001 | Lereclus |
| 6,995,007 | B2 | 2/2006 | Gunner et al. |
| 7,541,173 | B2 | 6/2009 | Bramucci et al. |
| 2007/0087423 | A1 | 4/2007 | Murakami et al. |

OTHER PUBLICATIONS

Li et al. (Phytopathology, vol. 85, No. 8, 1995, pp. 837-842).*
Kirchner et al. (MPMI, vol. 14, No. 11, 2001, pp. 1312-1318).*
Kaup et al. (MPMI, vol. 18, No. 10, 2005, pp. 1090-1098).*
Meighen (FASEB J., vol. 7, No. 11, pp. 1016-1022, Aug. 1993).*
Meletzus, D. et al., Evidence for Plasmid-Encoded Virulence Factors in the Phytopathogenic Bacterium *Clavibacter michiganensis* subsp. *michiganensis* NCPPB382, Journal of Bacteriolgoy, Apr. 1993, pp. 2131-2136, 175 (7).
Metzler, M.C. et al., The status of molecular biological research on the plant pathogenic genus *Clavibacter*, FEMS Microbiology Letter, 1997, pp. 1-8, 150.
Németh, J. et al., Development of immunofluorescence colony staining (IFC) for detection of *Xanthomonas campestris* pv. vesicatoria and *Clavibacter michiganensis* subsp. *michiganensis* in tomato seeds, Seed Sci. & Technol., 2006, pp. 85-100, 34.
Nissinen, R. et al., *Clavibacter michiganensis* subsp. *sepedonicus* Elicits a Hypersensitive Response in Tobacco and Secretes Hypersensitive Response-Inducing Protein(s), Phytopathology, 1997, pp. 678-684, 87(7).
Pastrik, K-H. et al., Identification and Differentiation of *Clavibacter michiganensis* Subspecies by Polymerase Chain Reaction-based Techniques, J. Phytopathology, 1999, pp. 687-693, 147.
Paynter, C.D. et al., The use of bioluminescence for monitoring in planta growth dynamics of a *Pseudomonas syringae* plant pathogen, European Journal of Plant Pathology, 2006, pp. 363-366, 115.
Poysa, V. et al., Evaluation of tomato breeding lines resistant to bacterial canker, Canadian Journal of Plant Pathology, 1993, pp. 301-304, 15.
Rai, P.V. et al., Phytotoxic Glycopeptides Produced by *Corynebacterium michiganense* II. Biological Properties, Phytopathology, pp. 53-57, 59.
Raj, S.N. et al., Seed bio-printing with *Pseudomonas fluorescens* isolates enhances growth of pearl millet plants and induces resistance against downy mildew, International Journal of Pest Management, Jan.-Mar. 2004, pp. 41-48, 50(1).
Rajashekara, G. et al., Temporal analysis of pathogenic events in virulent and avirulent *Brucella melitensis* infections, Cellular Microbiology, 2005, pp. 1459-1473, 7(10).
Ricker, M.D. et al., Effect of Secondary Spread of *Clavibacter michiganensis* subsp. *michiganensis* on Yield of Northern Processing Tomatoes, Plant Disease, Apr. 1993, pp. 364-366, 77(4).
Santos, M.S. et al., A rapid and sensitive detection of *Clavibacter michiganensis* subsp. *michiganensis* in tomato seeds by polymerase chain reaction, Seed Sci. & Technol., 1997, pp. 581-584, 25.
Schreiber, F. et al., Environmentally relevant concentrations of pharmaceuticals influence the initial adhesion of bacteria, Aquatic Toxicology, 2008, pp. 227-233, 87.
Shaw, J.J. et al., Development of a Vibrio Bioluminescence Gene-Set to Monitor Phytopathogenic Bacteria During The Ongoing Disease Process in a Non-Disruptive Manner, Biotechnology, Jun. 1986, pp. 560-564, 4.
Shaw, J.J. et al., Transposon Tn4431 Mutagenesis of *Xanthomonas campestris* pv. campestris: Characterization of a Nonpathogenic Mutant and Cloning of a Locus for Pathogenicity, Molecular Plant-Microbe Interactions, 1988, pp. 39-45, 1(1).
Shaw, J.J. et al., Use of Bioluminescence for Detection of Genetically Engineered Microorganisms Released into the Environment, Applied and Environmental Microbiology, Jan. 1992, pp. 267-273, 58(1).
Shirakawa, T. et al., Ecology and control of Tomato Bacterial Canker and Detection Methods of Its Pathogen, JARQ, 1991, pp. 27-32, 25.

(Continued)

*Primary Examiner* — Hope Robinson
(74) *Attorney, Agent, or Firm* — Standley Law Group LLP

(57) ABSTRACT

*Clavibacter michiganensis* subsp. *michiganensis* (Cmm) is an important Gram-positive-bacterial pathogen that infects tomato plants causing wilting and cankers and leading to severe economic losses in commercial tomato production worldwide. In order to visualize the infection process of Cmm in germinating seeds, bioluminescent Cmm strains were constructed by transforming the lux reporter gene into the bacterium. A vector pXX2 was constructed by inserting a modified promoterless lux-operon to a Cmm transposon mutagenesis vector, pKGT452Cβ. After electroporation, pXX2 carrying the $Cmx^r$::luxABCDE::Tn1409 cassette resulted in insertion of lux-operon into the Cmm chromosome. The virulent, stable, constitutively bioluminescent strain BL-Cmm17 was selected for further characterization of growth properties and inoculation on tomato seeds. Using this bioluminescent strain, Cmm colonization dynamics of germinating seeds were monitored in real-time using the in vivo imaging system (IVIS).

6 Claims, 5 Drawing Sheets

OTHER PUBLICATIONS

Ślusarski, C. et al., Evaluation of Chemical and Biological Control Methods for Their Potential to Reduce Bacterial Canker of Tomato in a Greenhouse Stonewool Cultivation System, Acta Hort, 2005, pp. 299-304, 698.

Stewart, G.S.A.B. et al., *Lux* genes and the applications of bacterial bioluminescence, Journal of General Microbiology, 1992, pp. 1289-1300, 138.

Strider, D.L., Bacterial Canker of Tomato Caused by *Corynebacterium michiganense*, A Literature Review and Bibliography, 1969, 81 pages.

Szittner, R. et al, Nucleotide Sequence, Expression, and Properties of Luciferase Coded by *Lux* Genes from a Terrestrial Bacterium, The Journal of Biological Chemistry, 1990, pp. 16581-16587, 265(27).

Theodoro, G.D.F. et al., In Vitro and in Vivo Action of Chemicals on *Clavibacter michiganensis* Subsp. *michiganensis*, Causal Agent of the Bacterial Canker of Tomato, Scientia Agricola, Jul./Sep. 2000, pp. 439-443, 57(3).

Tsiantos, J., Transmission of Bacterium *Corynebacterium michiganense* pv. *michiganense* by Seeds, J. Phytopathology, 1987, pp. 142-146, 119.

Uematsu, T. et al., Relationship between inoculation methods and seed infection with tomato canker bacteria, *Corynebacterium michiganense*, Ann. Phytopath. Soc. Japan., 1977, pp. 412-418, 43.

Utkhede, R. et al., Biological treatments to control bacterial canker of greenhouse tomatoes, BioControl, 2004, pp. 305-313, 49.

Van Alfen, N.K., Reassessment of Plant Wilt Toxins, Annu. Rev. Phytopathol., 1989, pp. 533-550, 27.

Wallis, F.M. et al., Ultrastructural histopathology of tomato plants infected with *Corynebacterium michiganense*, Physiological Plant Pathology, 1977, pp. 333-342, 11.

Wang, C. et al., Transposome mutagenesis of an integral membrane transporter of *Corynebacterium matruchotii*, Biochemical and Biophysical Research Communications, 2006, pp. 953-960, 340.

Weitz, H.J. et al., Construction of a modified mini-Tn5 *luxCDABE* transposon for the development of bacterial biosensors for ecotoxicity testing, FEMS Microbiology Letters, 2001, pp. 159-165, 197.

Winson, M.K. et al., Engineering the *luxCDABE* genes from *Photorhabdus luminescens* to provide a bioluminescent reporter for constitutive and promoter probe plasmids and mini-Tn5 constructs, FEMS Microbiology Letters, 1998, pp. 193-202, 163.

Alarcón, C. et al., Protein(s) from the Gram-Positive Bacterium *Clavibacter michiganensis* subsp. *michiganensis* Induces a Hypersensitive Response in Plants, Phytopathology, 1998, pp. 306-310, 88(4).

Bermpohl, A. et al., Exopolysaccharides in the pathogenic interaction of *Clavibacter michiganensis* subsp. *michiganensis* with tomato plants, Microbiol. Res., 1996, pp. 391-399, 151(4).

Brumbley, S.M. et al., Transformation and Transposon Mutagenesis of *Leifsonia xyli* subsp. *xyli*, Causal Organism of Ratoon Stunting Disease of Sugarcane, Molecular Plant-Microbe Interactions, 2002, pp. 262-268, 15(3).

Carlton, W.M. et al., Effects of Pruning on Tomato Plants Supporting Epiphytic Populations of *Clavibacter michiganensis* subsp. *michiganensis*, Plant Disease, Jul. 1994, pp. 742-745, 78(7).

Carlton, W.M. et al., Ingress of *Clavibacter michiganensis* subsp. *michiganensis* into Tomato Leaves Through Hydathodes, Phytopathology, 1998, pp. 525-529, 88(6).

Chabot, R. et al., Root Colonization of Maize and Lettuce by Bioluminescent *Rhizobium leguminosarum* biovar phaseoli, Applied and Environmental Microbiology, Aug. 1996, pp. 2767-2772, 62(8).

Chang, R.J. et al., Dissemination of *Clavibacter michiganensis* subsp. *michiganensis* by Practices Used to Produce Tomato Transplants, Phytopathology, 1991, pp. 1276-1281, 81(10).

Cirvilleri, G. et al., Differential expression of genes of *Pseudomonas syringae* on leaves and in culture evaluated with random genomic lux fusions, Molecular Ecology, 1994, pp. 249-257, 3.

Cirvilleri, G. et al., Short Communication, Luciferase Genes as a marker for *Pseudomonas corrugata*, Journal of Plant Pathology, 2000, pp. 237-241, 82(3).

Cirvilleri, G. et al., Internalization and Survival of *Pseudomonas corrugata* from Flowers to Fruits and Seeds of Tomato Plants, Internalization and Survival of *Pseudomonas, Pseudomonas syringae* Pathovars and Related Pathogens, 2008, pp. 73-79.

Craney, A. et al., A synthetic *luxCDABE* gene cluster optimized for expression in high-GC bacteria, Nudeic Acids Research, 2007, 1-10, 35(6).

Daferera, D.J. et al., The effectiveness of plant essential oils on the growth of *Botrytis cinerea, Fusarium* sp. and *Clavibacter michiganensis* subsp. *michiganensis*, Crop Protection, 2003, pp. 39-44, 22.

De León, L. et al, Detection of *Clavibacter michiganensis* subsp. *michiganensis* in tomato seeds using immunomagnetic separation, Journal of Microbiological Methods, 2006, pp. 141-149, 67.

De Weger, L.A., et al., Use of Bioluminescence Markers to Detect *Pseudomonas* spp. in the Rhizosphere, Applied and Environmental Microbiology, Dec. 1991, pp. 3641-3644, 57(12).

Dhanvantari, B.N., Effect of seed extraction methods and seed treatments on control of tomato bacterial canker, Canadian Journal of Plant Pathology, 1989, pp. 400-408, 11.

Dreier, J. et al., Southern Hybridization and PCR for Specific Detection of Phytopathogenic *Clavibacter michiganensis* subsp. *michiganensis*, Phytopathology, 1995, pp. 462-468, 85(4).

Dreier, J. et al., Characterization of the Plasmid Encoded Virulence Region pat-1 of Phytopathogenic *Clavibacter michiganensis* subsp. *michiganensis*, Molecular Plant-Microbe Interactions, 1997, pp. 195-206, 10(2).

Eichenlaub, R. et al., *Clavibacter michiganensis*, A Group of Gram-Positive Phytopathogenic Bacteria, Plant-Associated Bacteria, 2006, pp. 385-421.

Eppo, *Clavibacter michiganensis* subsp. *michiganensis*, European and Mediterranean Plant Protection Organization, 2005, pp. 275-283, 35.

Fan, J. et al., High-throughput quantitative luminescence assay of the growth in planta of *Pseudomonas syringae* chromosomally tagged with *Photorhabdus luminescens luxCDABE*, The Plant Journal, 2008, pp. 393-399, 53.

Fatmi, M. et al., Semiselective Agar Medium for Isolation of *Clavibacter michiganensis* subsp. *michiganensis* from Tomato Seed, Phytopathology, 1988, pp. 121-126, 78(1).

Fatmi, M. et al., Seed Treatments for Eradicating *Clavibacter michiganensis* subsp. *michiganensis* from Naturally Infected Tomato Seeds, Plant Disease, Apr. 1991, pp. 383-385, 75(4).

Fatmi, M. et al., Survival of *Clavibacter michiganensis* ssp. *michiganensis* in infected tomato stems under natural field conditions in California, Ohio and Morocco, Plant Pathology, 2002, pp. 149-154, 51.

Felise, H.B. et al., An Inhibitor of Gram-Negative Bacterial Virulence Protein Secretion, Cell Host & Microbe, Oct. 16, 2008, pp. 325-3.

Francis, K.P. et al., Monitoring Bioluminescent *Staphylococcus aureus* Infections in Living Mice Using a Novel *luxABCDE* Construct, Infection and Immunity, Jun. 2000, pp. 3594-3600, 68(6).

Francis, K.P. et al., Visualizing Pneumococcal Infections in the Lungs of Live Mice Using Bioluminescent *Streptococcus pneumoniae* Transformed with a Novel Gram-Positive lux Transposon, Infection and Immunity, May 2001, pp. 3350-3358, 69(5).

Fukui, R. et al., Relationship between Symptom Development and Actual Sites of Infection in Leaves of Anthurium Inoculated with a Bioluminescent Strain of *Xanthomonas campestris* pv. dieffenbachiae, Applied and Environmental Microbiology, Mar. 1996, pp. 1021-1028, 62(3).

Gartemann, K-H. et al., Isolation and Characterization of IS1409, an Insertion Element of 4-Chlorobenzoate-Degrading *Arthrobacter* sp. Strain TM1, and Development of a System for Transposon Mutagenesis, Journal of Bacteriology, Jun. 2001, pp. 3729-3736, 183(12).

Gartemann, K-H. et al., *Clavibacter michiganensis* subsp. *michiganensis*: first steps in the understanding of virulence of a Gram-positive phytopathogenic bacterium, Journal of Biotechnology, 2003, pp. 179-191, 106.

Gitaitis, R.D. et al., Induction of a Hypersensitivelike Reaction in Four-o'clock by *Clavibacter michiganensis* subsp. *michiganensis*, Plant Disease, Jan. 1990, pp. 58-60, 74(1).

Gitaitis, R.D. et al., Detection of *Clavibacter michiganensis* subsp. *michiganensis* in Symptomless Tomato Transplants, Plant Disease, Aug. 1991, pp. 834-838, 75(8).
Gleason, M.L. et al., Survival and Dissemination of *Clavibacter michiganensis* subsp. *michiganensis* in Tomatoes, Phytopathology, 1991, pp. 1519-1523, 81(12).
Gleason, M.L. et al., Recent Progress in Understanding and Controlling Bacterial Canker of Tomato in Eastern North America, Plant Disease, Nov. 1993, pp. 1069-1076,77(11).
Hadas, R. et al., Comparison of extraction procedures and determination of the detection threshold for *Clavibacter michiganensis* ssp. *michiganensis* in tomato seeds, Plant Pathology, 2005, pp. 643-649, 54.
Hakkila, K. et al., Reporter Genes *lucFF, luxCDABE, gfp*, and *dsred* Have Different Characteristics in Whole-Cell Bacterial Sensors, Analytical Biochemistry, 2002, pp. 235-242, 301.
Hardy, J. et al., Extracellular Replication of *Listeria monocytogenes* in the Murine Gall Bladder, Science, Feb. 6, 2004, pp. 851-853, 303.
Hausbeck, M.K. et al., Effect of Bactericides on Population Sizes and Spread of *Clavibacter michiganensis* subsp. *michiganensis* on Tomatoes in the Greenhouse and on Disease Development and Crop Yield in the Field, Phytopathology, 2000, pp. 38-44, 90(1).
Hutchens, M. et al., Applications of bioluminescence imaging to the study of infectious diseases, Cellular Microbiology, 2007, pp. 2315-2322, 9(10).
Jahr, H. et al., Interactions between *Clavibacter michiganensis* and its host plants, Environmental Microbiology, 1999, pp. 113-118, 1(2).
Jahr, H. et al., The Endo-β-1,4-glucanase CelA of *Clavibacter michiganensis* subsp. *michiganensis* is a Pathogenicity Determinant Required for Induction of Bacterial Wilt in Tomato, Molecular Plant-Microbe Interactions, 2000, 13(7).
Kamoun, S. et al., A Plant-Inducible Gene of *Xanthomonas campestris* pv. campestris Encodes as Exocellular Component Required for Growth in the Host and Hypersensitivity on Nonhosts, Journal of Bacteriology, Sep. 1990, pp. 5165-5172, 172(9).
Kaneshiro, W.S. et al., Differentiation of *Clavibacter michiganensis* subsp. *michiganensis* from seed-borne saprophytes using ELISA, Biolog and 16S rDNA sequencing, European Journal of Plant Pathology, 2006, pp. 45-56, 116.
Kaup, O. et al., Identification of a Tomatinase in the Tomato-Pathogenic Actinomycete *Clavibacter michiganensis* subsp. *michiganensis* NCPPB382, Molecular Plant-Mocrobe Interactions, 2005, pp. 1090-1098, 18(10).
Kirchner, O. et al., A Highly Efficient Transposon Mutagenesis System for the Tomato Pathogen *Clavibacter michiganensis* subsp. *michiganensis*, 2001, pp. 1312-1318, 14(11).
Kozukue, N. et al., Dehydrotomatine and α-Tomatine Content in Tomato Fruits and Vegetative Plant Tissues, Journal of Agricultural and Food Chemistry, 2004, pp. 2079-2083, 52.
Kuhajek, J.M. et al., A Rapid Microbioassay for Discovery of Novel Fungicides for *Phytophtora* spp., Phytopathology, 2003, pp. 46-53, 93(1).
Lewis Ivey, M.L. et al., Evaluation of Hot Water Seed Treatment for the Control of Bacterial Leaf Spot and Bacterial Canker on Fresh Market and Processing Tomatoes, Acta Hort, pp. 197-204, 695.
Louws, F.J. et al., rep-PCR-Mediated Genomic Fingerprinting: A Rapid and Effective Method to Identify *Clavibacter michiganensis*, Phytopathology, pp. 862-868, 88(8).
Meighen, E.A., Bacterial bioluminescence: organization, regulation, and application of the *lux* genes, The FASEB Journal, Aug. 1993, pp. 1016-1022, 7.
Meletzus, D. et al., Transformation of the Phytopathogenic Bacterium *Clavibacter michiganensis* subsp. *michiganensis* by Electroporation and Development of a Cloning Vector, Journal of Bacteriology, Jan. 1991, pp. 184-190, 173(1).

* cited by examiner

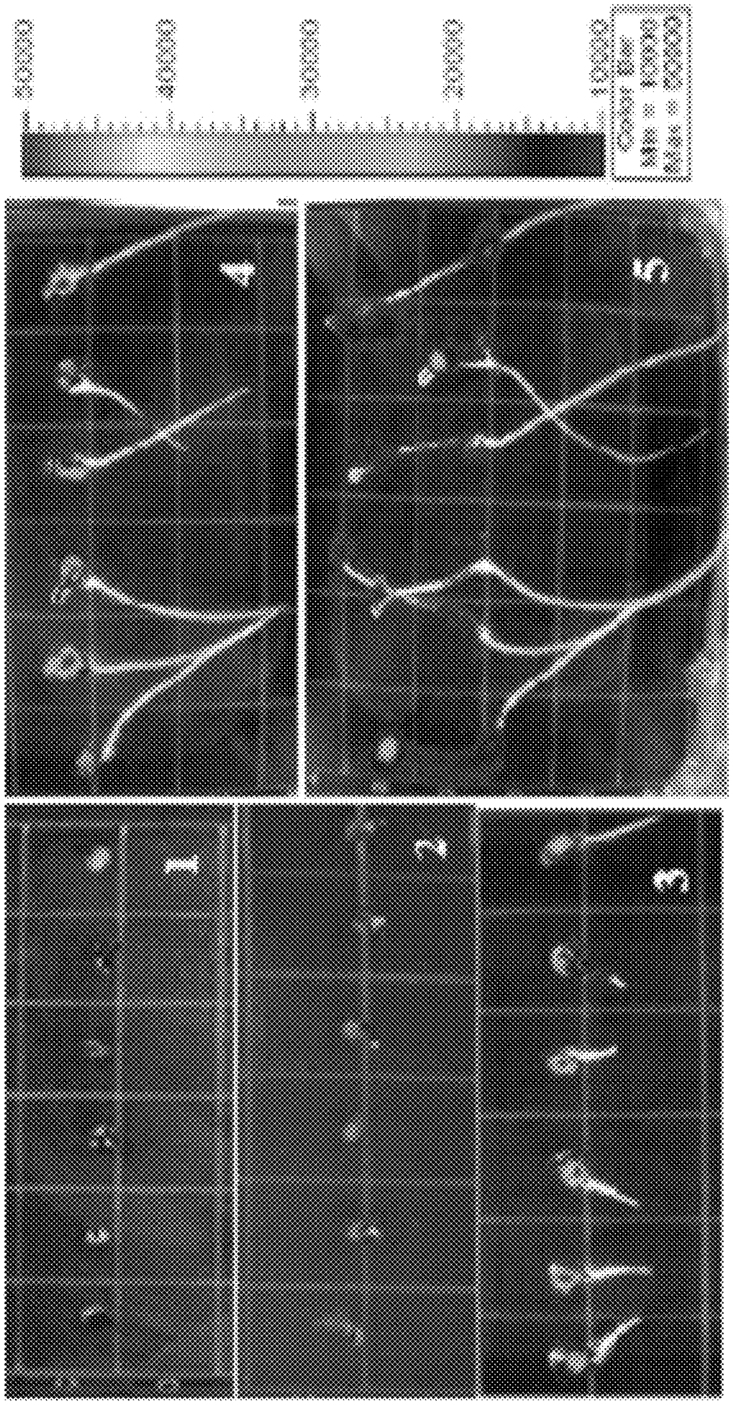
FIG—5

METHODS AND COMPOSITIONS RELATING TO BIOLUMINESCENT MICROORGANISMS

CROSS-REFERENCE TO RELATED APPLICATIONS

This application claims the benefit of priority to U.S. Provisional Patent Application No. 61/083,783, filed Jul. 25, 2008, which is hereby incorporated by reference in its entirety.

TECHNICAL FIELD

Exemplary embodiments relates to compositions and methods for analyzing bacterial pathogens. More particularly, embodiments relate to bioluminescent reporter bacteria for studying plant pathogens.

BACKGROUND OF THE ART

Tomato, one of the major vegetables, is widely cultivated in the world. In 2004, the production of tomato worldwide reached 120 million metric tons. The United States ranks second in tomato production with 428,900 acre of planted area, and total value was over 2 billion dollars in 2006. In the US, Ohio ranks third for both processing (6,400 acres) and fresh tomato production (6,700 acres) with total value of 125 million dollars in 2006. *Clavibacter michiganensis* subsp. *michiganensis* (Cmm), the bacterial pathogen of tomato canker, causes severe economic losses in commercial tomato production in the US and worldwide. Loss of yield is mainly due to defoliation, wilting and death of plants, reduced fruit size, and lesions on fruit. The disease was first discovered in a Michigan greenhouse in 1909 and many occurrences have been reported since then in North America. Bacterial canker is considered by the greenhouse tomato industry, which produces about 35% of all tomatoes sold in supermarkets and similar venues in North America, to be the most important and costly disease it must manage. Cmm is a quarantined pathogen in Europe and infected greenhouse and field plantings must be destroyed. Severe epidemics may cause 80% yield loss and according to the 2005 EPPO report tomato canker is present almost in all tomato production areas around the world. Bacterial canker is very difficult to control once it has been established in a planting, and to date there are no antibiotics or bactericides available to kill Cmm in the plant and prevent its spread to other plants.

An important means of disease spread is through infected seed and seedlings. Even a low transmission rate (0.01%) from seed to seedling can cause an epidemic of the disease under favorable conditions. Tomato seedlings are usually kept in a nursery for 4-6 weeks before transplanting to either greenhouse or field. As the density of seedlings is very high, the bacteria are easily spread through irrigation and leaf-to-leaf contact. Some infected young plants die soon after transplanting but many survive with epiphytic populations of Cmm that may spread to other plants. The mechanism of seed to seedling transmission of Cmm and the significance of its epiphytic phase in the ecology and epidemiology of the disease are still not fully understood.

SUMMARY OF THE INVENTION

This and other unmet advantages are provided by the methods and compositions described and shown in more detail below.

Exemplary embodiments comprise a method of studying pathogen transmission in a plant using a bioluminescent reporter bacteria, the method comprising the following steps: a) obtaining pathogenic bacteria from an infected plant; b) introducing into the bacteria a nucleic acid that encodes a bioluminescent reporter protein under conditions whereby the nucleic acid encoding the bioluminescent reporter protein is taken up by, stably integrated into the genome of, and expressed in the bacteria, wherein the bioluminescent reporter protein does not naturally occur in the bacteria; c) contacting a plant or plant seed with bioluminescent reporter bacteria obtained by steps a) and b); and d) monitoring bacterial colonization of the plant or plant seed in real-time by detecting in vivo luminescence signals on the plant or plant seed; wherein an amount of photons emitted correlates with a biomass of living pathogenic bacteria.

In various embodiments, the gram-positive pathogenic bacterium is a *Clavibacter* strain. Preferrably, the strain is a *Clavibacter michiganensis* subsps. *michiganensis*. The plant or plant seed may be a fully developed plant or plant part, a seedling, and/or seed. In a preferred embodiment, the bioluminescent reporter protein is constitutively expressed.

Embodiments also include methods for identifying compounds that inhibit the growth of pathogenic *Clavibacter* bacteria. Exemplary embodiments include a method of identifying a compound that inhibits pathogenic bacteria, the method comprising: a. providing a plant or seed colonized by bioluminescent reporter bacteria that expresses a bioluminescent reporter protein; b. contacting the plant or seed with a test compound; c. imaging the plant or seed to detect luminescence; and d. correlating a reduction in luminescence with an antibacterial effect of the test compound; wherein the bioluminescent reporter bacteria are mutants of the pathogenic bacteria. In various embodiments, the pathogenic bacteria are a *Clavibacter michiganensis* strain.

Various embodiments comprise mutant *Clavibacter michiganensis* bacteria. The mutant bacteria comprise an integrated nucleic acid that encodes a bioluminescent reporter protein. Preferrably, the nucleic acid that encodes the reporter protein is a lux construct. In exemplary embodiments, the reporter protein is constitutively expressed. In at least one embodiment, the nucleic acid comprises the nucleotide sequence of SEQ ID NO: 2 or a degenerate variant of SEQ ID NO: 2.

At least one embodiment is directed to an isolated nucleic acid vector comprising the nucleotide sequence of SEQ ID NO: 1 or a degenerate variant of SEQ ID NO: 1.

BRIEF DESCRIPTION OF THE DRAWINGS

A better understanding of the present invention will be obtained from a reading of the following detailed description and the accompanying drawings wherein identical reference characters refer to identical parts and in which:

FIG. 5 shows Cmm colonization (using the BL-Cmm 17 bioluminescent strain) dynamics of germinating seeds monitored in real-time using the in vivo imaging system (IVIS). The process was monitored daily for five days (1-5).

SEQUENCE DESCRIPTIONS

Figure 1:
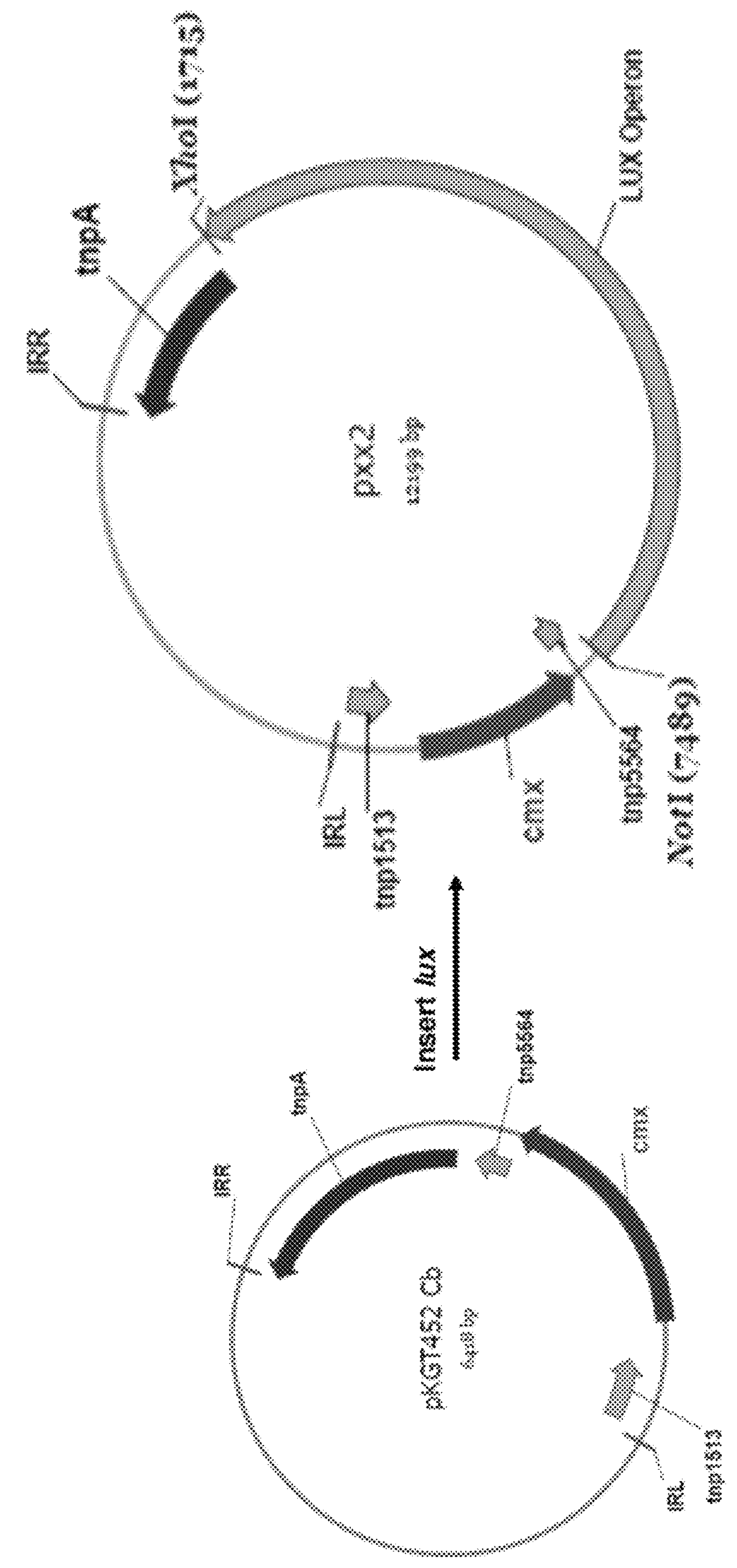
FIG. 1 is a schematic showing construction of the pXX2 vector (SEQ ID NO: 1) carrying the cassette Cmxr:luxABCDE::Tn1409 which integrates randomly into the Cmm chromosome.

The following sequences conform with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. 1.822.

TABLE 1

Relevant Plasmids and Nucleic in the Examples

| Nucleic Acids | Description | SEQ ID Nos |
|---|---|---|
| pXX2 | pKGT452Cβ Containging G- lux-operon. Ap, Cmx; 12.2 Kb | SEQ ID NO: 1 |
| Lux Operon | The lux-operon in pXen5 modified by adding an upstream Gram-positive ribosome binding site (AGGAGG) | SEQ ID NO: 2 |
| pXen5 | Source for G+ lux-operon, , Ery, Kan; 18.3 Kb | SEQ ID NO: 3 |
| pKGT452Cβ | Tn1409 Cβ; tnpA and cmx; Ap, Cmx; 6.4 Kb; | SEQ ID NO: 4 |

TABLE 2

Oligonucleotides in the Examples

| Name | Sequence[a] | Purpose |
|---|---|---|
| LuxpXen5F (EcoRI) (SEQ ID NO: 5) | ATAAAAGAATTCGACTCCTGTGAAATGATC | Amplify the lux-operon and kanamycin gene from pXen5 |
| LuxpXen5R (SalI) (SEQ ID NO: 6) | AAAAAACTCGACCGGATGTACTTCAGAAAAGA | |
| pKGT1F (NotI) (SEQ ID NO: 7) | AAAAAAGCGGCCGCATCACGCCGCTAGAGCTT | Inverse PCR amplification of pKGT452Cβ to clone G+ lux operon from pXen5 |
| pKGT1R (XhoI) (SEQ ID NO: 8) | AAAAAACTCGAGTCAGAGAAGGTGAGGGCCTC | |
| kanF (SEQ ID NO: 9) | GAAGCGTTTGATAGTTAAGT | For confirmation of EZ::TN<lux-kan> integration into chromosome |
| kanR (SEQ ID NO: 10) | GGTACTAAAACAATTCATCC | |
| LuxpXen5F2 (NotI) (SEQ ID NO: 11) | ATAAAAGCGGCCGCGAAACAGCTATGACCATGAT | Amplify lux-operon without kanamycin gene from pXen5 |
| LuxpXen5 R2 (XhoI) (SEQ ID NO: 12) | AAAAAACTCGAGTTATTATTTCCCTCCTCGAC | |
| pKGT2F (XhoI) (SEQ ID NO: 13) | AAAAAACTCGAGATCACGCCGCTAGAGCTTGG | Inverse PCR amplification of pKGT452Cβ to clone G– lux operon from pXen13 |
| pKGT2R (NotI) (SEQ ID NO: 14) | AAAAAAGCGGCCGCTCAGACAAGGTGAGGGCCTC | |
| CmxF (SEQ ID NO: 15) | AGAGTACTGCCGACGCCGA | For confirmation of Tn1409 integration into chromosome |
| CmxR (SEQ ID NO: 16) | ACTGTCGATCCTGCTCTCCG | |
| Xu3F (SEQ ID NO: 17) | GGATTTGTCGGGGTGTTTCG | For mapping insertion site of Tn1409-lux in Cmm genome |
| Xu3R (SEQ ID NO: 18) | CGGCCCCACAGAAGCAATTA | |

[a]Restriction sites added in the original sequences are underlined.

DETAILED DESCRIPTION OF A PREFERRED EMBODIMENT

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety for all purposes. In case of conflict, the present specification, including definitions, will control. In addition, the materials, methods, and examples are illustrative only and not intended to be limiting.

*Clavibacter michiganensis* subsp. *michiganensis* (Cmm) is an important Gram-positive-bacterial pathogen that infects tomato plants causing wilting and cankers and leading to severe economic losses in commercial tomato production worldwide. An important means of spreading disease is through infected seeds and seedlings. However, little is known regarding the mechanism of seed and seedling infection. In order to visualize the infection process of Cmm in germinating seeds, bioluminescent Cmm strains were constructed by transforming the lux reporter gene into the bacterium. A vector pXX2 (SEQ ID NO: 1) was constructed by inserting a modified promoterless lux-operon to a Cmm transposon mutagenesis vector, pKGT452Cβ. After electroporation, pXX2 (SEQ ID NO: 1) carrying the $Cmx^r$::luxABCDE::Tn1409 cassette resulted in insertion of lux-operon into the Cmm chromosome.

In total, 19 bioluminescent Cmm mutants were obtained. The mutants varied in light production, but all tested strains induced hypersensitive response with *Mirabilis jalapa* (four o'clock plant) and caused wilting in tomatoes. The virulent, stable, constitutively bioluminescent strain BL-Cmm17 was selected for further characterization of growth properties and inoculation on tomato seeds.

Using this bioluminescent strain, Cmm colonization dynamics of germinating seeds were monitored in real-time using the in vivo imaging system (IVIS). Disclosed Cmm strains colonized the seed's hypocotyl and the cotyledon at an early stage of germination. Importantly, the novel embodiments using bioluminescent Cmm will help elucidate the dynamics of plant infections with this and other important and difficult-to-control pathogens.

Because the lux transposon vector embodied herein may be useful in the other subspecies of agriculturally important *C. michiganensis* as well as other members of actinomycetes, embodiments may have significant impact in understanding pathogenesis of disease caused by other pathogens, for example, actinomycetes.

The following definitions and abbreviations are to be used for the interpretation of the claims and the specification.

The term "gene" refers to a nucleic acid fragment that is capable of being expressed as a specific protein, optionally including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

As used herein the term "coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of effecting the expression of that coding sequence (i.e., that the coding sequence is under the transcriptional control of the promoter). Coding sequences can be operably linked to regulatory sequences in sense or antisense orientation The term "expression", as used herein, refers to the transcription and stable accumulation of sense (mRNA) or antisense RNA derived from the nucleic acid fragment of the invention. Expression may also refer to translation of mRNA into a polypeptide.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The terms "plasmid" and "vector" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation vector" refers to a specific vector containing a foreign gene and having elements in addition to the foreign gene that facilitates transformation of a particular host cell.

As used herein the term "codon degeneracy" refers to the nature in the genetic code permitting variation of the nucleotide sequence without affecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

Standard recombinant DNA and molecular cloning techniques used here are well known in the art and are described by Sambrook, J., Fritsch, E. F. and Maniatis, T., Molecular Cloning: A Laboratory Manual, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., Experiments with Gene Fusions, Cold Spring Harbor Laboratory Cold Press Spring Harbor, N.Y. (1984); and by Ausubel, F. M. et al., Current Protocols in Molecular Biology, published by Greene Publishing Assoc. and Wiley-Interscience (1987).

EXAMPLES

The following examples are included to demonstrate preferred embodiments of the invention. It should be appreciated by those skilled in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Bacteria Strains and Growth Conditions

Bacterial strains and plasmids used in the examples are listed in Table 3.

TABLE 3

Bacterial strains and plasmids used in this study

| Strains or plasmids | Description | Reference or source |
|---|---|---|
| Strains | | |
| *Clavibacter michiganensis* subsp. *michiganensis* C290 | Wild type virulent strain of Cmm isolated in Ohio | Lab collection |
| *C. michiganensis* subsp. *michiganensis* A300 | Wild type virulent strain of Cmm isolated in Ohio | Lab collection |
| *E. coli* DH5α | Used in cloning experiments | Invitrogen |
| *E. coli* ER2925 | dam/dcm Methylation negative strain | NEB |

TABLE 3-continued

Bacterial strains and plasmids used in this study

| Strains or plasmids | Description | Reference or source |
|---|---|---|
| Plasmids | | |
| pXen5 | Source for G+ lux-operon, , Ery, Kan; 18.3 Kb | Xenogen, Francis et al, 2001. |
| pXen13 | Source for G− lux-operon from *P. luminescence* Amp; 8.7 Kb | Xenogen |
| pMod3 | Containing EZ::TN; 2.8 Kb | Epicentre |
| pKGT452Cβ | Tn1409 Cβ; tnpA and cmx; Ap, Cmx; 6.4 Kb; | Kirchner et al. 2001 |
| pUC4K | Source of kanamycin resistence marker, Kan, Ap | Amersham |
| pUWGR4 | Containing EZ::TN, G− promoterless lux operon, Kan; 10 Kb | Rajashekara et al, 2005 |
| pXX1 | pMod3 Containing EZ::TN containing G+ promoterless lux. Kan 9.3 Kb | the examples |
| pXX2 (SEQ ID NO: 1) | pKGT452Cβ Containging G− lux-operon. Ap, Cmx; 12.2 Kb | the examples |
| pXX3 | pKGT452Cβ Containing G+ lux-operon. Ap, Cmx; 12.3 Kb | the examples |

Kan, Kanamycin resistance; Ap, Ampicillin resistance; Cmx, Chloramphenicol resistance; Ery, Erythromycin.

*C. michiganensis* subsp. *michiganensis* strains A300 and C290 were isolated from infected plants in Ohio and belonged to BOX-PCR fingerprint type A and type C, respectively (Louws et al, 1998). Depending on the assay, Cmm strains were grown in yeast dextrose calcium carbonate broth (YDC) (Bacto, Franklin Lakes, N.J.), nutrient-broth yeast extract broth (NBY) (Bacto, Franklin Lakes, N.J.), or tryptone broth with yeast (TBY, containing 10 g/liter of tryptone, 5 g/liter of yeast extract, and 5 g/liter of NaCl; pH7.5). *E. coli* strains (DH5a and ER2925) were grown on LB at 37° C. Antibiotics Ampicillin (150 μg/ml), chloramphenicol (20 μg/ml), and kanamycin (50 μg/ml) were added to the media as necessary.

Construction of Plasmids pXX1, pXX2 and pXX3

Both pXen5 and pXen13 (Xenogen Corporation, Alameda, Calif.) carry promoterless lux-operon (luxCDABE) originally isolated from *Photorhabdus* luminescence. The lux-operon in pXen5 had been modified by adding an upstream Gram-positive ribosome binding site (AGGAGG) upstream of each lux genes for optimal expression of lux genes in Gram positive bacteria (Francis et al. 2001). To construct pXX1, the lux-operon and kanamycin resistance gene from pXen5 were amplified by a long range, high fedility PCR using Herculase Polymerase (Stratagene, Calif.) and the LuxpXen5F/LuxpXen5R primers. Appropriate restriction sites (EcoRI and SalI) were inserted in the primers to facilitate cloning. Oligonucleotides were designed using Vector NTI® software and commercially synthesized by Integrated DNA Technologies (Skokie, Ill.). All the oligonucleotides used in the examples are listed in Table 2. Appropriate restriction sites were included in the primers to facilitate cloning. The amplified PCR product was digested and ligated to a similarly digested Tn5 transposon construction vector pMod 3 (Epicentre, Madison, Wis.) in order to generate the plasmid pXX1. Consequently, pXX1 carries EZ::TN<lux-kan> cassette insert, which is flanked by the Tn5 transposon mosaic ends.

pXX2 (SEQ ID NO: 1) was constructed by amplifying the lux-operon from pXen-5 with primers LuxpXen5

F2/LuxpXen5R2. Inverse PCR was performed on the Cmm mutangensis vector pKGT452Crβ (Kirchner et al, 2001) with pKGT1 F and pKGT1R primers that were designed to amplify all but the region of lux insertion. Appropriate restriction sites (NotI and XhoI) were added to the PCR primers to facilitate cloning (Table 2). The inverse PCR product was digested and ligated to the similarly digested lux-operon (SEQ ID NO: 2) from pXen5, generating pXX2 (SEQ ID NO: 1), which carries Gram-positive Lux ($Cmx^r$:: luxABCDE:: Tn1409).

To construct pXX3, the lux-operon was obtained by digesting pXen13 with NotI and XhoI and ligated to similarly digested inverse PCR product of the plasmid pKGT452Crβ amplified using the pKGT2F/pKGT2R primers. The pXX3 carries Gram-negative Lux ($Cmx^r$:: luxABCDE::Tn1409). Recombinant plasmids pXX1, pXX2 (SEQ ID NO: 1) and pXX3 were transformed to *E. coli* DH5a and subsequently propagated in the dam and dcm deficient *E. coli* strain, ER2925, (New England Biolabs, Beverly, Mass., U.S.A.), since the use of unmethylated DNA improves transformation efficiency in Cmm (Kirchner et al, 2001).

Mutagenesis and Isolation of Bioluminescent Cmm

Bioluminescent Cmm strains were generated by electroporation of either the modified EZ::TN transposomes from pXX1, containing the aforementioned Gram-positive promoterless luxABCDE genes (G+ lux) or pUWGR4, containing the Gram-negative promoterless luxCDABE (Gram− lux) (Rajashekara et al, 2005) or by directly electroporating the suicide vectors containing the modified transposon Tn1409 (pXX2 and pXX3). Before electroporation, the EZ::TN transposome was prepared as described by the manufacturer (Epicentre, Madison, Wis.), while pUWGR4 and pXX1 were digested with PvuII and the resulting 6.8 kb and 7.3 kb linear DNA fragments, respectively containing the Gram− lux and Gram+ lux with $kan^R$ genes, were gel purified using QIAquick gel extraction kit (Qiagen, Valencia, Calif.). Two μl of each purified DNA (100 ng/μl) were mixed separately with 4 μl of EZ::TN transposase (Epicentre, Madison, Wis.) and 2 μl of 100% glycerol, achieving a total volume of 8 μl per reaction. Following incubation for 30 min at room temperature, the transposome complexes were stored at −20° C. until further use.

Electrocompetent Cmm 290 aliquots were prepared as described previously (Kirchner et al, 2001). Briefly, bacteria were grown to $OD_{600}$ 0.5-0.7 in TBY broth at 25° C. Cells were then pretreated with 2.5% glycine for 2 h and harvested by centrifugation at 9,000×g for 10 min, which was followed by washing with sterile ice cold distilled water for three times and 10% glycerol twice. The cell pellet was then resuspended in 15% glycerol to $1/250^{th}$ of the original volume. Transformation was achieved by mixing 100 μl of electrocompetent Cmm cells with 1-2 μl of the EZ::TN transposome complex or suicide plasmids pXX2 or pXX3 (1 μg each) and electroporation was performed in a 0.2-cm cuvette, using a Gene Pulser Xcell electroporator (BioRad, Hercules, Calif.) with the following setting: Voltage, 2.5 kV; capacitance, 25 μF; resistance, 600Ω. Immediately after electroporation, the cells were mixed with 0.6 ml of SB medium, (tryptone at 10 g/liter, yeast extract at 5 g/liter, NaCl at 4 g/liter, 91.1 g sorbitol, 0.4 g $MgCl_2$, 0.3 g $CaCl_2$, pH 7.5), transferred into a 10 ml sterile disposable tube and incubated shaking (140 rpm) for 3 h at 28° C. Finally, the cells were spread on SB agar plates containing kanamycin (50 μg/ml) or chloramphenicol (10 μg/ml) and incubated for 4 to 7 days at 28° C. The $kan^R$ or $cm^R$ colonies were recovered and streaked onto NBY plates containing appropriate antibiotics and screened for bioluminescence using a sensitive charge-coupled device (CCD) camera (Xenogen Corporation, Alameda, Calif.). The bioluminescent colonies were purified and stored for further analysis.

PCR Analysis of Bioluminescent Cmm Strains

To confirm the integration of the target DNA, PCR analysis was performed on all recovered colonies. After electroporation with pXX1, colonies were tested using the KanF/KanR primers that target part of the kananmycin resistant gene. Additionally, colonies recovered after electroporation with pXX2 (SEQ ID NO: 1) or pXX3 were tested for the presence of the chloramphenicol gene using primers CmxF/cmxR. PCR was performed on genomic DNA obtained from mutants using Taq PCR Master Mix kit (Qiagen, Valencia, Calif.).

Analysis of Bioluminescence

To quantify the amount of bioluminescence emitted by the transformed Cmm, isolates were grown in NBY broth containing the appropriate antibiotics with aeration at 28° C. for 48 h. Three replicates (100 μl) of each culture were then transferred to a black 96-well plate and bioluminescence was quantified using In vivo imaging system (IVIS) (Xenogen Corporation, Alameda, Calif.). The photon amount of each well (photons/s) was normalized for background luminescence by subtracting the value of a control well, containing NBY broth only. The O.D. was measured and the photon amount was divided by the O.D. to normalize for culture cell density. Highly bioluminescent colonies were selected for further studies.

The Hypersensitive Response (HR) Assay

The bioluminescent strains were tested for virulence in four o'clock (*Mirabilis jalapa*) plants (HR test). Briefly, four o'clock plants were grown in clay pots. Bacterial suspensions ($10^8$ cfu/ml) were prepared in sterile water and injected into fully expanded leaves of four o'clock plants using needle-less syringes, ensuring that the bacteria would infiltrate into intercellular spaces. Typically, the wild type virulent Cmm produces HR-characteristic necrotic lesions in the infiltrated areas within 36-48 hours (Gitaitis, 1990). For each strain, four injections were applied on one leaf and inoculated plants were placed for up to 48 hours in a greenhouse with a 14 hour light/10 hour dark photoperiod. The wild type Cmm strain C290 and sterile water were used as positive and negative controls, respectively.

Pathogenicity Assay

The inoculation of tomato seedlings with bioluminescent Cmm strains was performed as previously described by Poysa (1993). The cotyledons of tomato seedlings were clipped using dissecting scissors that had been dipped in a Cmm suspension ($10^8$ cfu/ml). Tomato seedlings (n=3) were inoculated with each strain and monitored for symptoms for three weeks. Furthermore, virulence was assessed by determining the number of plants that exhibited wilting symptoms within three weeks after inoculation. To quantify the bacterial numbers in infected tomato plants, stem samples from three plants were taken 3 cm above the cotyledons. Samples were ground in 3 ml phosphate buffer (pH=7.4, 10 mM) and centrifuged at 1000 rpm for 3 min. The supernatant was serially diluted and plated onto NBY agar plates that were supplemented with chloramphenicol (10 μg/ml). For samples inoculated with C290, serial dilutions were spread onto D2ANX (a semi-selective medium for Cmm). Colony counts were recorded on the fifth day. The bacterial numbers (cfu/g) were calculated as number of colonies*dilution*3 ml/weight of sample tissue. The HR and pathogenicity assays were repeated twice.

Assessing In Vitro Growth, Constitutive Expression of Bioluminescence, and Stability of Tn1409 Insertion in a Virulent Bioluminescent Cmm Strain To assess constitutive lux expression, the strongly bioluminescent BL-Cmm17 strain was grown on NBY plates for 48 h at 28° C. and then transferred to 50 ml NBY broth in a 200 ml flask and incubated at 28° C. with shaking (160 rpm). At different time points, the $OD_{600}$ and total bioluminescent counts were determined. Relative light units were determined by log transformation of average radiance (photons/second/$cm^2$).

Stability of the transposon insertion was verified by growing the BL-Cmm strain without antibiotic selection in 5 ml NBY broth at 28° C. for 72 h, which was repeated for a total of five rounds (with 5 μl for each re-inoculation). After five rounds of growth, the culture was diluted in NBY broth and plated on NBY agar plates without antibiotics and incubated at 28° C. for 72 h. To assess the stability of insertion, 50 colonies from three replicates were randomly selected and patched on to NBY agar plates with chloramphenicol. The growth and bioluminescence of each colony was assessed to determine the stability of insertion.

The in vitro growth of the bioluminescent BL-Cmm17 was determined in both rich NBY medium as well as a Cmm minimal medium (Alarcon, et al, 1998). BL-Cmm17 strain growing on NBY plates for 48 h at 28° C. were inoculated into a 200 ml flask containing 50 ml NBY broth or the Cmm minimal medium and incubated at 28° C. with shaking at 160 rpm for 72 h. The Bacterial growth was monitored by measuring the $OD_{600}$ from 1 ml culture at different times. C290 was used as a control throughout the experiment.

Mapping of the Tn1409 Insertion Site

Genomic DNA was extracted from both BL-Cmm6 and BL-Cmm17 using a MasterPure Gram Positive DNA purification kit (Epicentre, Madison, Wis.) and the insertion site in each strain was determined by bi-directional sequencing using the primers Xu3F/Xu3R. Sequencing was performed using dye terminators at a DNA sequencing core facility, (The Plant-Microbe Genomic Facility, The Ohio State University). Sequences were compared to the Cmm genome to determine the site of insertion.

Seed Inoculation with Bioluminescent Cmm Strains

The BL-Cmm17 was tested on tomato seeds using different inoculation methods. Healthy tomato seeds (cv. OH9242) were inoculated either by soaking seeds in bacterial suspension ($10^8$ cfu/ml) for 5 min under vacuum or by dropping 10 μl of bacterial suspension ($10^8$ to $10^5$ cfu/ml) onto each seed. Seeds that were inoculated with sterilized water were used as controls. After inoculation, the seeds were air dried and placed on a moisture filter paper or in a glass tube with water agar (0.7%) or a square petri dish with water agar. The seeds were allowed to germinate in the dark at 28° C. Bioluminescent Cmm colonization of germinating seeds was monitored daily using the IVIS and bacteria were isolated from $5^{th}$ day seedlings that exhibited luminescence signals.

Isolation of the Bioluminescent Cmm Strain

In order to generate a Cmm strain, we desired stable insertion of lux operon as well as constitutive expression of bioluminescence. Stable insertion is important for in planta real time studies even in the absence of antibiotic selection. Because of the lack of tools for genetic manipulation of Cmm, we tried several approaches to integrate lux genes into Cmm chromosome. Since the lux-operon in pXen13 was originally derived from the Gram-negative bacterium, *Photorhabdus luminescence*, it might not be expressed efficiently in Cmm, a Gram-positive bacterium. Consequently, the lux-operon was modified by incorporating AGGAGG, a Gram-positive ribosome binding site, upstream of each luxABCDE genes (Francis et al., 2000). The plasmid pXen-5 carries the lux-operon (SEQ ID NO: 2) optimized for expression in Gram positive bacteria. Initially we tried Tn5 based transposon mutagenesis approach that has been successfully used in *Corynebacterium matruchotii* that is closely related to Cmm. The plasmids, pUWGR4 and pXX1 carried a promoterless Gram negative lux-operon and a modified Gram positive lux-operon, respectively. The mosaic ends flanking these operons can be recognized by Tn5 transposase. After the electroporation of the Tn5:lux complexes into Cmm strains A300 and C290, a total of 84 colonies were recovered on SB plates supplemented with kanamycin (50 μg/ml). However, only about 50% of the recovered colonies grew when introduced to fresh plates and none were bioluminescent when screened by the CCD camera. PCR analysis targeting the kanamycin gene in resulting colonies showed that they lacked the transposon. Further, the negative control, Cmm electroporated without an EZ::TN<lux-Kan> casette, also resulted in colonies that grew on the kanamycin-containing plates, which suggested that Cmm strains used in electroporation might have exhibited spontaneous kanamycin resistance. These results suggest that the Tn5 transposon system is not suitable for Cmm mutagenesis.

Recently, Gartemann et al. developed an efficient mutagenesis system for Cmm using Tn1409. The Tn1409 containing vector pKGT452Cβ was modified to contain either Gram positive (pXX2) (FIG. 1) or Gram negative lux operon (pXX3). After electroporation of pXX3 into Cmm strains, three colonies were recovered, which were analyzed by PCR and were to harbor the chloromphenicol resistance gene (data not shown), indicating the presence of the transposon in their genome. However, none of these strains were bioluminescent, which is likely due to the lack of expression of Gram negative lux in the Gram positive bacteria. However, when transposon vector, pXX2 (SEQ ID NO: 1) containing Gram positive lux was electroporated in to Cmm, bioluminescent colonies were successfully recovered. The transformation efficiency of Cmm with pXX2 (SEQ ID NO: 1) was about an average of two transformants per 1 μg of vector DNA, which was similar when using either Cmm C290 or A300. Twenty-six putative transformed colonies grew on SB plates after electroporation. However, only 19 colonies (BL-Cmm1 to 19) were bioluminescent when screened by the IVIS. Upon further analysis using PCR, both the $cmx^R$ gene and the lux-operon were detected in the genomes of the bioluminescent strains (data not shown).

Figure 2:
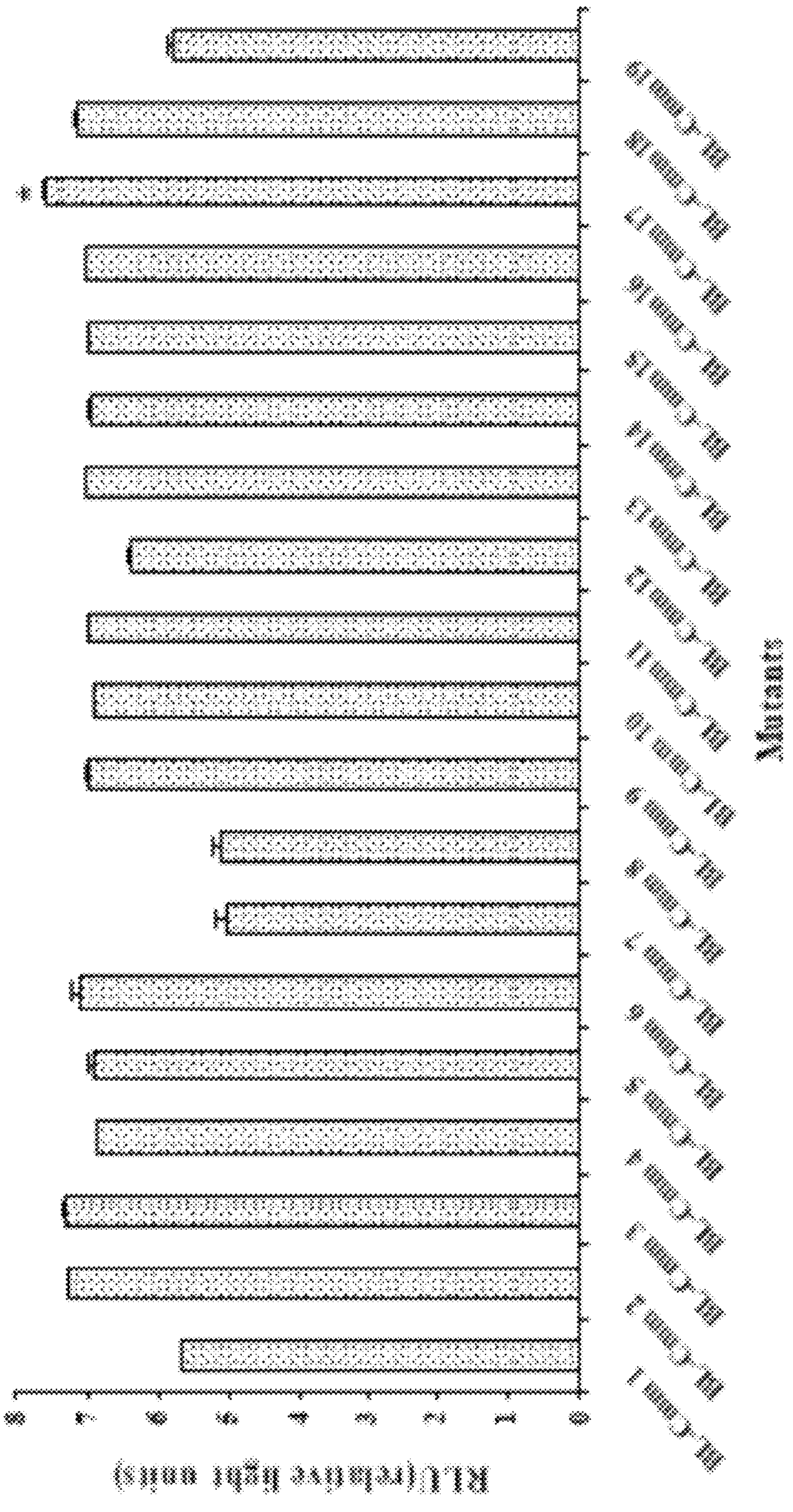
FIG. 2 shows a graph of the bioluminescence in various mutant Cmm strains. The light intensity of $10^8$ CFU from each strain was measured from late log phase cultures and divided by OD to normalize for differences due to culture growth

To evaluate the amount of bioluminescence in these mutants, light intensity of $10^8$ CFU from each strain was measured from late log phase cultures and divided by OD to normalize for differences due to culture growth (FIG. 2). Data analysis showed that BL-Cmm 17 exhibited significantly higher bioluminescence compared to other strains. Since Tn1409 randomly integrates lux into the Cmm genome, the lux operon might be regulated by upstream promoters with different expression levels. Consequently, variations in the lux operon expression are expected, leading to the observed differences in bioluminescence emitted by different bioluminiscnet strains.

Figure 3:
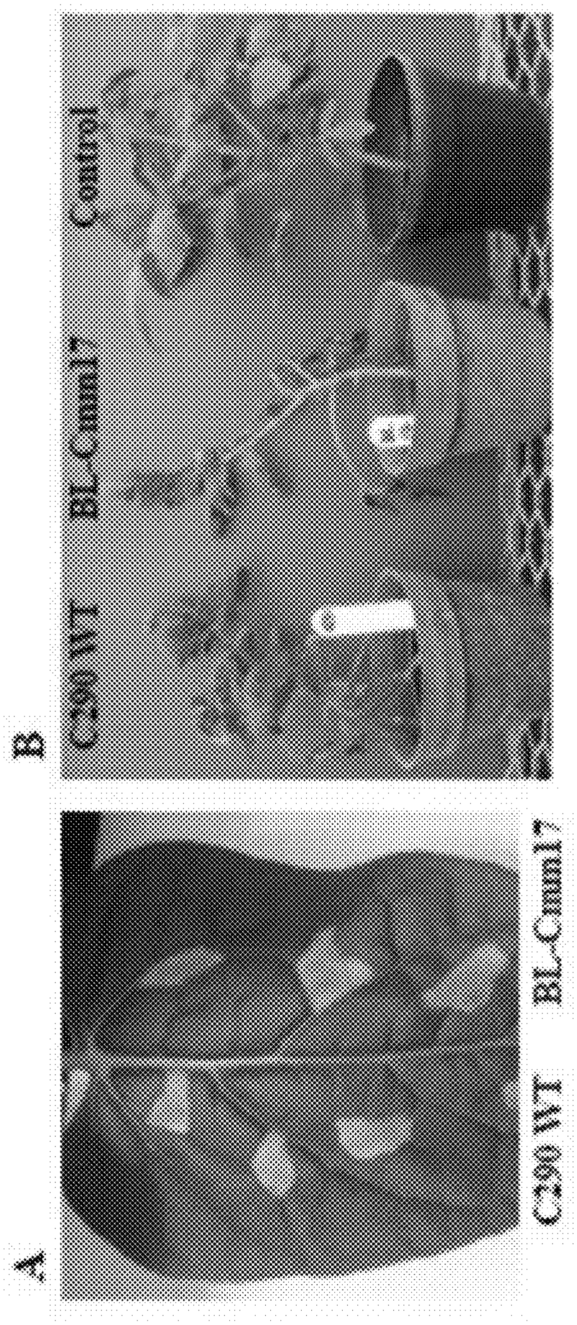
FIG. 3 is a photograph demonstrating that BL-Cmm 17 induced a strong hypersensitive response on four o'clock seedlings similar to WT C290, indicating its their virulence was similar to that of the wild type (see also, Table 4)

The Impact of the Lux Insertion on the Virulence of the Bioluminescent Cmm Strains Since Tn1409 is randomly inserted into the Cmm genome (Kirchner,et al. 2001), the lux-operon might affect genes that are essential for pathogenicity. Therefore, it was necessary to test the bioluminescent strains and verify that the insertion did not affect virulence. For this purpose, the pathogenicity of the bioluminescent strains was tested using four'o clock plants, which exhibits a hypersensitive response (HR) when challenged with Cmm (Gitatis, 1990). Nine bioluminescent strains (BL-Cmm1 to 8, and 17) that emitted a relatively higher and different range of light intensity were selected for this assay and all isolates induced a strong HR on four o'clock plant, indicating that their virulence was similar to that of the wild type strain (Table 4, FIG. 3).

TABLE 3

HR and virulence assays of bioluminescent Cmm strains.

| Strains | HR[a] | Virulence[b] | Log CFU/g in planta[c] |
|---|---|---|---|
| BL-Cmm1 | + | 6/6 | 9.57 |
| BL-Cmm2 | + | 5/6 | 10.63 |
| BL-Cmm3 | + | 6/6 | 10.55 |
| BL-Cmm4 | + | 6/6 | 8.77 |
| BL-Cmm5 | + | 5/6 | 9.88 |
| BL-Cmm6 | + | 6/6 | 9.11 |
| BL-Cmm7 | + | 6/6 | 9.23 |
| BL-Cmm8 | + | 6/6 | 8.77 |
| BL-Cmm17 | + | 6/6 | 9.43 |
| C290 | + | 6/6 | 9.08 |
| Water | – | 0/6 | 0.00 |

[a]+, Positive for HR reaction, –, Negative for HR reaction;
[b]Number of wilting plants/total inoculated plants.
[c]Mean population of bacteria recovered from stem tissue of three replicates samples; no significant difference was observed as tested by T-test at $P = 0.05$.

To further test pathogenicity, the nine BL-Cmm strains (1 to 8, and 17) were inoculated into tomato seedlings and all isolates caused of plant wilting. However, some strains resulted in a lower number of wilting plants compared to the wild type Cmm 290 (data not shown). In addition, the number of bacteria in the stem tissue of the seedlings was determined to further characterize the colonization ability of the bioluminescent strains. The number of the bioluminescent strains retrieved from the stem tissue was similar to that of the wild type C290, suggesting that the ability of the BL strains to colonize the vascular tissue was not impacted by the lux-insert. Since the bacteria recovered from the stem tissues were still strongly bioluminescent when checked by the IVIS, it was concluded that lux-insert was stable in these strains.

Growth Analysis of Virulent and Bioluminescent Cmm Strains

Figure 4:
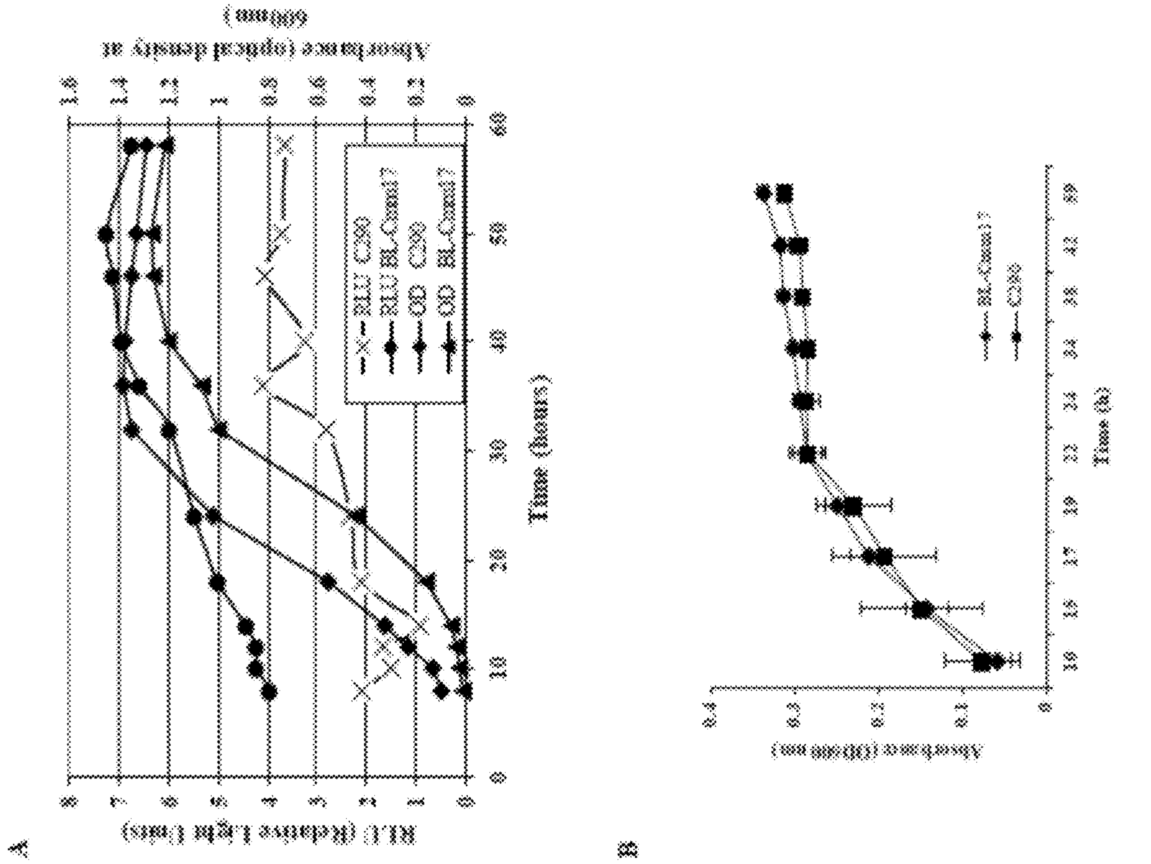
FIG. 4 are graphs demonstrating that in vitro growth of BL-Cmm17 was similar to that of its parent strain C290: Bioluminescence increased as BL-Cmm17 grew in log phase and started to decrease when its growth reached the stationary phase suggesting a constitutive expression of the lux (4A); the similar growth pattern of BL-Cmm17 and C290 was observed in minimal media indicating that lux insertion in BL-Cmm did not have any auxotrophic effect on the growth and survival of BL-Cmm 17 (4B).

Because of its relatively strong bioluminescent signals and the similarity of its virulence to C290, BL-Cmm17 was selected for further characterization. The in vitro growth of BL-Cmm17 was similar to that of its parent strain C290, both displaying a duplication time of 4.5 h (FIG. 4A). Bioluminescence increased as BL-Cmm17 grew in log phase and started to decrease when its growth reached the stationary phase suggesting a constitutive expression of the lux (FIG. 4A). Furthermore, the similar growth pattern of BL-Cmm17 and C290 was observed in minimal media indicating that lux insertion in BL-Cmm did not have an auxotrophic effect on the growth and survival of BL-Cmm 17 (FIG. 4B). Since the stability of the lux insertion in BL-Cmm17 is important for accurate real-time visualization of the bacterium, BL-Cmm17 was subjected to several rounds of non-selective growth and then re-grown on media containing chlormaphenicol and tested for bioluminescence. All colonies retrieved after replicating the experiment twice were resistant to chloramphenicol and were bioluminescent after five rounds of growth in NBY broth with no antibiotic. Therefore, the incorporation of the lux-operon in BL-Cmm17 was considered stable.

Mapping the Insertion Site of Lux-Operon in Bioluminescent BL-Cmm 17

In order to characterize the insertion site of the lux-operon in the genome of BL-Cmm17, chromosomal DNA was isolated from the strain and sequenced with theXu3F/Xu3R primers. The sequences representing the strain and the pXX2 (SEQ ID NO: 1) vector were highly aligned with over 90% of identical sequences suggesting the whole vector integration into the genome of BL-Cmm17. This is not surprising and was found to happen occasionally when using this mutagenesis system in Cmm (personal communication with Dr. Karl-Heinz Gartemann). Therefore, further analysis is needed to identify the insertion sites. However, since the insertion of the lux-operon did not influence the growth of BL-Cmm 17 and the expression of the lux-operon was stable and constitutive, it can be assumed that the lux-operon was inserted dowmstream of a strong promoter without disturbing any housekeeping or essential virulence genes in the BL-Cmm17 genome.

Monitoring the Colonization of Bioluminescent Cmm in Germinating Tomato Seeds

To assess the usability of the BL-Cmm17 for monitoring in vivo infection processes in real-time, tomato seeds were inoculated with this strain. Over 100 seeds were tested using different geminating supplies, including filter papers in petri dishes, glass tubes containing water agar and square plates with water agar. The pattern of colonization was similar regardless of the germination supplies. Specifically, after inoculating the seeds with BL-Cmm17, the bacteria maintained their activity on the seed coat (FIG. 5). However some bacteria attached to the hypocotyls as it elongated during germination, while few luminescence signals were detected in the root (FIG. 5). On day 5, most of the bacterial cells aggregated in the cotyledons and hypocotyls, highlighting the early colonization pattern of Cmm on tomato seedlings.

Efficiency of Transmission of Cmm During Propagation and the Influence of Environmental Factors on its Transmission (Prophetic) (a) Seed to seedling transmission: Seed to seedling transmission of Cmm will be studied using rootstock ('Maxifort') and scion (open-pollinated indeterminate variety) seed infested with BL-Cmm17 harvested from plants inoculated by 1) flower inoculation and 2) injection of peduncles of very young fruit. Open-pollinated varieties will be used to minimize variation in progeny of inoculated plants. In our experience 90-100% of seed produced by this method are infected with Cmm. The level (CFU/seed) of infestation of individual seeds will be assessed by measuring luminescence; a standard curve will first be produced plotting photons/s vs. CFU from individual seeds. Seeds (five per treatment/sampling time; each seed is a replication) with estimated low ($<10^2$ CFU/seed), medium ($10^2$-$10^4$ CFU/seed) and high ($>10^4$ CFU/seed) BL-Cmm17 loads (non-infested seed will be used as a control) will be germinated under varying temperature and moisture conditions, in germination medium. Care will be taken to prevent seedling-to-seedling contamination. Seed-to-seedling movement/colonization by BL-Cmm17 will be visualized nondestructively daily using IVIS until stem diameters reach 1.5-2 mm (approx. 2 weeks). Five randomly selected seedlings/variable will be extracted individually and the extracts plated on YDC+chloramphenicol (10 ug/ml). Luminescent colonies will be counted. Extracts will also be tested by Cmm ELISA (Agdia, Inc., Elkhart, Ind.).

(Prophetic) (b) Transmission by grafting and topping: The influence of Cmm inoculum concentration and rootstock vs. scion colonization may be evaluated using seedlings generated as described above except that the optimal environmental conditions for Cmm transmission will be used. Preliminary studies will determine the timing of planting the scion and rootstock (rootstock usually requires 2-5 additional days). Rootstock and scion seedlings with the four inoculum loads (0, low, medium and high) will be grafted onto healthy plants. Hands, tools and work area will be sanitized after each graft.

Seedlings will be incubated under standard conditions for 2-3 weeks (Rivard and Louws 2006). Colonization of seedlings by BL-Cmm17 will be followed using IVIS daily for 2-3 weeks. Five plants per treatment will be sampled randomly every five days and BL-Cmm17 culturing and ELISA, except that population counts will be made from 5 mm stem segments cut from the base of the plant to 2 cm above the graft union. At least five plants per treatment will be maintained in a greenhouse after graft healing and observed for disease symptoms. Topping studies will be designed to determine the population threshold for Cmm transmission by topping, the extent of spread from individual infected plants, and the influence of cutting tool (vs. hand pinching) on transmission. BL-Cmm17-infected plants will be grown from seed infested with 0, low, medium and high Cmm populations, or will be inoculated by injection with the pathogen at similar population levels. The goal is to obtain plants with different internal population counts. It will likely be necessary to produce a large number of plants (approx. 20-30 at each inoculum level) to achieve this goal. For simplicity, non-grafted 4-6 week-old plants will be topped by hand pinching or knife/blade, then 10 healthy plants will be topped sequentially with disinfecting hands or blades. Plants will be labeled in sequence and the extent of transmission will be determined using IVIS every 2-3 days and by symptoms, culturing and ELISA at the end of the experiment (3-4 weeks later). A 1-cm section from the cut end of the topped portion of each plant will be extracted and the extract will be dilution plated and tested by ELISA. Colony counts will be made after 4-5 days.

Identify Novel Small Molecules Inhibitory to Cmm that can Protect Plants from Bacterial Canker (Prophetic) (a) High-throughput chemical screen for Cmm inhibitors. A library of >50,000 small molecule candidates will be screened for antimicrobial activity against BL-Cmm17 and naturally occurring strains of Cmm from the OSU culture collection. Compounds will be purchased from ChemBridge Corp. (San Diego, Calif., USA) and Enzo Life Sciences International, Inc. (Plymouth Meeting, Pa.). These libraries contain synthetic drug-like compounds as well as natural products with a molecular size generally in the range 250-500 Da and high chemical structure diversity, with tens of thousands of distinct chemical scaffolds. Antibiotics (ampicillin 150 μg/ml) and kanamycin (50 μg/ml) will be used as positive controls.

Compounds will be screened for antibacterial activity by bacterial growth-inhibition assays using a customized screening system in 96- or 384-well plates using a liquid-handling robot (Biomek3000; Beckman Coulter, Inc. Fullerton, Calif.). BL-Cmm17 will be cultured in TBY or other suitable medium to stationary phase, and then sub-cultured in the same medium (1:100) until it reaches an $OD_{600}$ of 0.5-0.7. These bacteria, in exponential growth phase, will be diluted to $OD_{600}$ of 0.05, and placed 200 μl/well into 96- or 384-well clear flat bottom plates. Compounds will be added at a final concentration of 25 μM. In all plates, the $OD_{600}$ will be measured before and after 24 h incubations at 28° C. with shaking. Negative controls (1% DMSO vehicle) and positive controls (antibiotics) will be run in each plate. Bacterial growth will be monitored by a CCD camera using IVIS. In addition, we will determine the $OD_{600}$ using a plate reader (Fisher Scientific). The percentage of bacterial growth inhibition will be determined as the percentage inhibition=100×($OD_{neg\ control}$−$OD_{test\ compound}$)/($OD_{neg\ control}$−$OD_{pos\ control}$). $EC_{50}$ values will be derived from analysis of concentration-response data, with serial dilutions of the active compounds.

To determine the effect of selected small molecules on different strains of Cmm, we will choose the five most promising small molecule inhibitors and evaluate their effect using a bacterial growth-inhibition assay by monitoring the $OD_{600}$ following exposure to different compounds as described above. Different Cmm strains (at least 200) will be cultured in TBY or other selected medium to stationary phase, and then sub-cultured in the same medium (1:100) until they reached an $OD_{600}$ of 0.5-0.7. These bacteria, which are in exponential growth phase, will be diluted to $OD_{600}$ of 0.05, and placed 200 μl/well into 96 or 384-well clear flat bottom plates. Selected compounds will be added at a final concentration of 25 μM. Plates will be incubated for up to 48 h at 28° C. with shaking. Negative controls (1% DMSO vehicle) and positive controls (antibiotics) will be run in each plate. Bacterial growth will be monitored by measuring the $OD_{600}$ at different times. All compounds will be screened in duplicate. We anticipate identifying small molecules that exhibit activity against all strains of Cmm.

(Prophetic) (b) Effect of selected small molecules on Cmm colonization of tomato seedlings. The effects of selected small molecules on colonization of tomato seedlings by Cmm will also be evaluated. Tomato plants (cv. OH9242-an inbred line) will be inoculated with BL-Cmm17 by spraying flowers or injecting peduncles and infested seed will be harvested. Seeds may also be artificially infested with the bacterium by vacuum infiltration ($10^8$ CFU/ml for 5 min) if necessary. Seeds will be distributed into 96-well plates and compounds will be added in a randomized complete block design to eight wells each at a final concentration of 25 μM, with control wells containing 1% DMSO. Plates will be incubated as described above for 5 days. The antibacterial effect of selected compounds will be determined by bioluminescent imaging (IVIS) each day and further confirmed by conventional CFU determination on a subset of four replicate germlings per treatment after 5 days. Another subset of four germlings per treatment, including non-treated and non-inoculated controls, with no visible bacterial colonization (no luminescence) will be transplanted individually into small pots and maintained in a greenhouse under warm, humid conditions for 4-6 weeks and assessed for symptoms. Plants will be drip irrigated individually under constant positive water pressure to avoid splashing and possible bacterial spread.

(Prophetic) (c) Effect of selected small molecules on bacterial canker development in production tomatoes (MSU). Finally, compounds that effectively inhibit bacterial canker symptom development in seedlings will be tested for activity in larger plants produced under conditions simulating commercial environments.

The following documents are hereby incorporated by reference (there is no admission thereby made with respect to whether any of the documents constitute prior art with respect to any of the claims):

Alarcón, C., Castro, J., Muñoz, F., Arce-Johnson, P., and Delgado, J. 1998. Protein(s) from the gram-positive bacterium *Clavibacter michiganensis* subsp. *michiganensis* induces a hypersensitive response in plants. Phytopathology 88:306-310.

Carlton, W. M., Braun, E. J., and Gleason, M. L. 1998. Ingress of *Clavibacter michiganisis* subsp. *michiganisis* into tomato leaves through hydathodes. Phytopathology 88:525-529.

Chang, R. J., Ries, S. M., and Pataky, J. K. 1991. Dissemination of *Clavibacter michiganensis* subsp. *michiganensis* by practices used to produce tomato transplants. Phytopathology. 81: 1276-1281.

Chabot, R., Antoun, H., Kloepper, J. W., Beauchamp, C. J. 1996. Root colonization of maize and lettuce by bioluminescent *Rhizobium leguminosarum* biovar. *phaseoli*. Appl Environ Microbiol 62:2767-72.

De Weger, L. A., Dunbar, P., Mahafee, W. F., Lugtenberg, J. J. and Sayler G. S. 1991. Use of bioluminescent markers to detect *Pseudomonas* spp. in the rhizosphere. Applied and environmental microbiology 57: 3641-3644.

Dreier J., Bermpohl A., and Eichenlaub, R. 1995. Southern hybridization and PCR for specific detection of phytopathogenic *Clavibacter michiganensis* subsp. *michiganensisngress* of *Clavibacter* michiganisis subsp.michiganisis into tomato leaves through hydathodes. Phytopathology 85: 462-468.

Dreier, J., Meletzus, D., and Eichenlaub, R. 1997. Characterization of the plasmid encoded virulence region pat-1 of phytopathogenic *Clavibacter michiganisis* subs *p. michiganisis*. Molecular Plant-Microbe Interactions 10: 195-206

Eichenlaub R., Gartemann, K. H., and Burger, A. 2006. *Clavibacter michiganensis*, A group of gram-positive phytopathogenic bacteria. Plant-Associated Bacteria. 385-421

Fan, J., Crooks C. and Lamb, C., 2008. High-throughput quantitative luminescence assay of the growth in planta of *Pseudomonas syringae* chromosomally tagged with *Photorhabdus luminescens* luxCDABE The Plant Journal 53: 393-399.

Fatmi, F. and Schaad, N. W. 2002. Survival of *Clavibacter michiganensis* ssp. *michiganensis* in infected tomato stems under natural field conditions in California, Ohio and Morocco. Plant Pathology 51:149-154.

Francis K. P., Joe, D., Bellinger-Kawahara, C. Hawkinson, M. J., Purchio, T. F., and Contag, P. R. 2000. Monitoring bioluminescent *Staphylococcus aureus* infections in living mice using a novel luxABCDE construction. Infection and Immunity 68: 3594-3600.

Gitaitis, R. D. 1990. Induction of a hypersensitive-like reaction in four o'clock by *Clavibacter michiganensis* subsp. *michiganensis*. Plant Dissease. 74:58-60.

Gleason, M. L., Gitaitis, R. D. and Ricker, M. D. 1993, Recent Progress in Understanding and Controlling Bacterial Canker of Tomato in Eastern North America. Plant Disease.

Hardy, J., Francis, K. P., DeBoer, M., Chu, P., Gibbs, K., and Contag, C. H. 2004. Extracellular replication of *Listeria monocytogenes* in the murine gall bladder. Science 303: 851-853.

Ivey, M. L. and Miller, S. A. 2005. Evaluation of hot water seed treatment for the control of bacterial leaf spot and bacterial canker on fresh market and processing tomatoes. Acta Hort. 695: 197-204.

Jahr, H., Dreier, J., Meletzus, D., Bahro, R., Eichenlaub, R., 2000. The endo-β-glucanase CelA of *Clavibacter michiganensis* subsp. *michiganensis* is a pathogenicity determinant required for induction of bacterial wilt of tomato. Molecular Plant-Microbe Interactions 13: 703-714.

Kaneshiro, W. S., Mizumoto, C. Y. and Alvarez, A. M. 2006. Differentiation of *Clavibacter michiganensis* subsp. *michiganensis* from seed-borne saprophytes using ELISA, Biolog and 16S rDNA sequencing. European Journal of Plant Path. 116:45-56.

Kaup, O., Grafen, I., Zellermann, E., Eichenlaub, R, and Gartemann, K. 2005. Identification of a tomatinase in the tomato-pathogenic actionmycete *Clavibacter michiganisis* subsp. *michiganisis*. NCPPB382. Molecular Plant-Microbe Interaction 18: 1090-1098.

Kirchner,O., Gartemann, K., Zellermann, E., Eichenlaub,R. and Burger, A. 2001. A highly efficient transposon mutagenesis system for the tomato pathogen *Clavibacter michiganensis* subsp. *michiganensis*. Molecular Plant-Microbe Interation 14(11): 1312-1318.

Louws, F., Bell, J., Medina-Mora, C., Smart, C. D., Opgenorth, D., Ishimarn, C., deBruijin, F. R., Hausbeck, M., and Fulbright, D. W. 1998. Rep-PCR-mediated genomic finger-printing: a rapid and effective method to identify *Clavibacter michiganensis* subsp. *michiganensis*. Phytopathology 88:862-868.

Meichen, E. A. 1993. Bacterial bioluminescence: organization, regulation, and application of the lux genes. The FASEB Journal, 7:1016-1022, Meletzus, D. and Eichenlaub, R. 1991. Transformation of the phytopathogenic bacterium *Clavibacter michiganense* subsp.*michiganense* by electroporation and development of a cloning vector. Journal of bacteriology 173: 184-190.

Meletzus, D., Bermpohl, A., Dreier, J. and Eichenlaub, R. 1993. Evidence for plasmid-encoded Virulence factors in the phytopathogenic bacterium *Clavibacter michiganense* subsp.*michiganense* NCPPB382. Journal of bacteriology 175: 2131-2136.

Metzler, M. C., Laine, M. J., and De Boer, S. H. 1997. The status of molecular biological research on the plant pathogenic genus *Calvibacter*. FEMS Microbiology Letters 150: 1-8.

Nissinen, R., Lai, F.-M., Laine, M. J., Bauer, P. J., Reilley, A., Li, X., De Boer, S. H., Ishimaru, C. A., and Metzlerm M. C. *Clavibacter michiganensis* subsp. *sepedonicus* Elicits a hypersensitive response in tobacco and secretes hypersensitive response-inducing proteins. 1997.

Pastrik K. H., and Rainey F. A. 1999, Identification and differentiation of *Clavibacter michiganensis* subspecies by polymerase chain reaction-based techniques. Journal of Phytopathology 147: 687-693.

Paynter, C. D., Salisbury, V. C., Arnold, D. L. and Jackson R. W. 2006. The use of bioluminescent for monitoring in planta growth dynamics of a *Pseudomomnas syringae* plant pathogens. European Journal of Plant Pathogen 115: 363-366.

Rajashekara, G., Glover, D. A., Krepps, M. and Splitter, G. A. 2005. Temporal analysis of pathogenic events in virulent and avirulent *Brucella melitensis* infections. Cellular Microbiology 7(10): 1459-1473.

Ricker, M. D. and Riedel, R. M. 1993, Effect of secondary spread of *Clavibacter michiganensis* subsp. *michiganensis* on yield of Northern Processing tomatoes. Plant Disease 77: 364-366.

Shaw, J. J., Dane, F., Geiger, D., Kloepper, J. W. 1992. Use of bioluminescence for detection of genetically engineered microorganims released into the environment. Appl Environ Microbiol 58:267-73.

Sousa, S., Cruz, L., Norskov, P., and Rasmussen, O. F. A rapid 1997. A rapid and sensitive detection of *Clavibacter michiganensis* subsp. *michiganensis* in tomato seeds by polymerase chain reaction. Seed science and technology, 25: 581-584.

Stewart, G. S, and Williams, P. 1992. lux genes and the applications of bacterial bioluminescence. *The Journal of general microbiology* 138: 289-300.

Strider, D. L. 1969. Bacterial canker of tomato, a literature review and bibliography. N.C. Agri. Exp. Stn. Tech. Bull. 193.

Tsiantos, J., 1987. Transmission of bacterium *Corynebacterium michiganense* pv. *michiganense* by seeds. J. Phytopathol. 119:142-146.

Uematsu, T., Fuji, H. and Ohata, K. 1977. Relationship between inoculation methods and seed infection with tomato canker bacteria. Ann Phytopath. Soc. Japan 43: 412-418.

Wang, C., Hays, B., Vestling, M. M., and Takayama, K. 2006. Transposome mutangenesis of an integral membrane trasporter in *Corynebacterium matruchotii*. Biochemical and Biophysical Research Communication, 340: 953-960.

Weitz H J, Ritchie J M, Bailey D A, Horsburgh A M, Killham K., Glover L A, 2001, Construction of a modified mini-Tn5 luxCDABE transposon for the development of bacterial biosensors for ecotoxicity testing. FEMS Microbiology Letters, Volume 197: 159-165.

Winson M. K., Swift, S., Hill, P. J., Sims C. M., Griesmayr, G., Bycroft B. W., Williams P., and Stewart, G. S. A. B. 1998 Engineering the luxCDABE genes from *Photorhabdus luminescens* to provide a bioluminescent reporter for constitutive and promoter probe plasmids and mini-Tn5 constructs. *FEMS Microbiology Letters* 163:193-202.

Other Embodiments

It is to be understood that while exemplary embodiments have been described in conjunction with the detailed description thereof, the foregoing description is intended to illustrate and not limit the scope of the invention, which is defined by the scope of the appended claims. For example, the vector pXX2 (SEQ ID NO: 1), may also be used for transformation of lux operon into other important pathogens facilitating the study of *Clavibacter* transmission, control, and plant interactions. Relevant pathogens include other important subspecies of *C. michiganensis*, including subsp. *insidiosus* (causes wilt and stunt on alfalfa), subsp. *nebraskensis* (cause wilt and leaf blight on corn), and subsp. *sepedonicus* (causes ring rot on potato) (Metzler et al. 1997; Kirchner et al. 2001). Therefore, embodiments apply broadly to the pathogenesis of disease caused by actinomycetes. Other aspects, advantages, and modifications are within the scope of the following claims.

What is claimed is:

1. A method of studying pathogen transmission in a plant or plant seed, the method comprising:

a) introducing into a *Clavibacter Michiganensis* strain a nucleic acid vector comprising the nucleotide sequence of SEQ ID NO: 1, wherein the nucleic acid encodes a bioluminescent reporter protein and wherein the nucleic acid is stably integrated into the genome and expressed in the *Clavibacter Michiganensis* strain;

b) contacting the plant or plant seed with the *Clavibacter Michiganensis* strain obtained from a); and c) monitoring bacterial colonization of the plant or plant seed in real-time by detecting in vivo luminescence signals on the plant or plant seed;

wherein an amount of photons emitted correlates with a biomass of living pathogenic bacteria.

2. An isolated mutant *Clavibacter michiganensis* strain, comprising an integrated nucleic acid that encodes a bioluminescent reporter protein, wherein the nucleic acid comprises the nucleotide sequence of SEQ ID NO:2.

3. The mutant *Clavibacter* strain of claim 2, wherein: the reporter protein is constitutively expressed.

4. An isolated nucleic acid comprising the nucleotide sequence of SEQ ID NO: 1.

5. A vector comprising the nucleic acid of claim 4.

6. A method of studying pathogen transmission in a plant or plant seed, the method comprising:

contacting the plant or plant seed with an isolated mutant *Clavibacter Michiganensis* strain comprising an integrated nucleic acid that comprises the nucleotide sequence of SEQ ID NO:2; and monitoring bacterial colonization of the plant or plant seed in real-time by detecting in vivo luminescence signals on the plant or plant seed;

wherein an amount of photons emitted correlates with a biomass of living pathogenic bacteria.

* * * * *

SEQUENCE LISTING

```
<160> NUMBER OF SEQ ID NOS: 18

<210> SEQ ID NO 1
<211> LENGTH: 12199
<212> TYPE: DNA
<213> ORGANISM: Artificial Sequence
<220> FEATURE:
<223> OTHER INFORMATION: Plasmid

<400> SEQUENCE: 1

cgaacgctgc ggccgaactc ggcttcaccg aacgggcctg gttcacgatg gtcacaggtc     60

tcggcgcggc tgttgatcca gaccgatcgc ttactcaagc agctgacctt gacggatctg    120

gccaagttca cccaggcgtg tgacgaccgc ggcgcccgga ccggcaagcg accaggtcgc    180

aggcggctgt gagccgaaga gaaagtttga agtcagacaa ggcgaacgac ggcgggccag    240

gtcatttgta attcgagacc tgcttggccg aacgcgcgct acgaacctca taaacagcaa    300

taggtagtct tgccgagggt gggcaatgag gctcttcaga attgagggtg tagtttcggt    360

ctgaatccgc cggattccag gagcgagcgg gctatgtagt tggtgaggtt ccggaacccg    420

agggctgagc cgcggaggtg ttccagtctc ccgttaattg cttctgtggg gccgttcgat    480

gttccgggcc gatcgaagta cgccagcacg tcttctgccc gtcgtttgag ggtccgcccc    540

agcgtcttga gctcggtgag agcggccggg acgcctgtgc tgatggaatt gaccactgcc    600

tgcatgagct tctttccttg gatgcggtcc tgctcccggt acgcggcaat catgcgctga    660

tagatgcccc agctggcttc gacctcgacg tgcgcatcgg tggcgaacaa gtcccgaagg    720

cgttggcgtt gtttgtcggt gagcaggtca gcacccgtgt gcagcgtccg cctcgctttg    780

tagagaggat cgccggcccg tccacgatgc ccgcacgttg cctgctgaac gcgtcgcctg    840

cagacatcga gtgcatcgcc tgccaagcgg atgacgtgga agggatccat gaccggaaca    900

gcctcgggaa gctcttcggc agcggcgctt ttgaagccgg agaatccgtc catggccacg    960

acttccaccc cttcccgcca cgcttcaggg cgttcgttca gccacgtggc gaagacctgc   1020

tttgagcggc cctcgaccat gtccagcagc cgggaagggc ccgtgccgtc acggatcggt   1080

gtcagatcga tgatgacggt gacgtacttg tccccgcggc gggtgtgccg ccaaacatgc   1140

tcatcaacac caatgacctt cactccatcg aagcggtgcg ggtcatcgat caatacgcgc   1200

cggccctcgg ccagaacggc gttgttcgcg gtattccacg acacgcccag gccctcggca   1260
```

-continued acccgggcca ccgtcagatg ctgacagacg atgccttcca atgcccagcg cagtccacgg 1320
cgggaaagct tcgctcttgg ttcagcagcc ttcgaggtct cctgccgcca cacataaccg 1380
caccccggtgc agcggtaacg tcggagcctc accagcaata tcgtgggccg ccaaccgaag 1440
ggttcatggc ccagccgccg ggtcacagta tcccgcggga tgccctcgca cccacatctg 1500
gaacaccact catcagcatc caccacacgg caggtaatga cagcacgatc agggtacaga 1560
cactgcccag tggcttccag gccgagctca tcgaggcgac agaatgtggt caggtcaggg 1620
cgctggagag tagcgttgga catgagggcc ttgcggtaga aaattcaaga tctagacaat 1680
ctgattctct cccgaggccc tcaccttgtc tgactcgagt tattatttcc ctcctcgact 1740
taactatcaa acgcttcggt taagcttaaa gcacaccctt tctgcgtcct cgtattgacg 1800
cgacgtaaaa tttcaacgag cacgccggga tacttaccat attctctgct aattatcccg 1860
acatcatcgg taacaataaa tgctggataa ctggttgctg acgcatccat ataactcatc 1920
aaccccggcg ttccatcagg tacaggtttc aacgtttcag gatcaagcgc tcgcgcatat 1980
acccacggcg gaacatgttt acgctgcatt tcatcctcaa agaaacaagt gttgagttca 2040
acttgattaa atatatctcg gatctgacta atatcactga gattgaaagt atcaaataaa 2100
agatgattga aatcatcacg tttcagagat tctttttcgt aacttttcca gccgcctccg 2160
gttatgatat aaaggctttt atctccagaa aatgagattt ttttatcttt catataatgg 2220
cagagtaaat aaataaagta tggcgaacca ataagacaaa gatctttccc ttgatttttt 2280
attcgttcaa gactattcaa tgttttaaca aaatctattc gttcttctgt tacggtaaat 2340
gtcgtaggat ataacaattc caccaaactc ataacatatt taaaccaaat attatgagca 2400
ttaaatctat ctggtcccaa attgactaat tctatttgat gatcaaacca actaccaaca 2460
tatttcatgc cataactcac agagcctaag agtctctcaa tacttaatct gtcacgcgcc 2520
acctgacttt ttaaaccatt cgtgccgcta ctggtaaacc aactttcaat ctcgttttcc 2580
tgagaagtta ataagcgagt aaacttaaaa accgatgttg ggaatacagg tatgtcatca 2640
atttccgtaa tattgtcatc tactttgtgt gcctgacagt agtgacgata ttctcgacaa 2700
tgtttataat gattacgaaa tgcatcaagc acaagtttct ttctgatttt ttcctgctcg 2760
tcgtaagacc acactaatgg atcgctcgaa aaaatcaaat catcaatttc tgagcttgct 2820
gtaatttctt gtttatcaac atatgaagtc atacctgttt tcctcctcga cttaagacag 2880
agaaattgct tgattttcaa tctcaattct cattcggcgt tcattgactg tcgcaatagt 2940
taaatgttca aatgacggtt cagtaatatc aacatcaata tccagatgat cattatccat 3000
cgcgatagcg gctttcgtaa ccgattgata aaaattgcgc aggaccacta aattttcact 3060
caagtcatgc gaacttccta acaaagaata tatcttgcat cgattactac gaatatttga 3120
taacaatgtg ataacttcat cttgcttgac ccaattatcg ttatttgcag taaaagcaat 3180
aaacggtata tcaagataca tcatgttatt aattgtagaa gctaaatctt cccaaccaaa 3240
atcaagacaa tctctcgcaa agacttcagc acccaattta tggccttcaa aatctagatt 3300
atccggcaat tcattaatgg gtagactgag ataatcaaac cctaaagctc tttcaagaga 3360
atatcttaag ttaacaacac cgactgcggt gattaaaaac gaagcattga tttcagatag 3420
gcttgcataa gctatccgcg cagataagct tgaagccaac ataccgaagt tatttatttt 3480
tcgtgtagtt aaccaatcaa ccactgctaa caagctctgc tttcctatag acattgtaaa 3540
ttcatcaatt gtccctgaac tcaatccaac gtggtgaagc gaatcatagc ggatcacatg 3600
aaatccattc cgcgataaat attccgccag accagcaaaa tgatccatcc tgcgggcaaa 3660

-continued accagacgca ataataatgg cattctttct ctttgggctg ttttcttctg gcagcgtttc 3720
ccaaacatga atttttttat ttccttcaac acaaataacg tggtcgatgg ttttatattt 3780
tgattcattt tccatacttt tactcctcct cgacttatgg gacaaataca aggaacttat 3840
cttcttccag gaatcgagtc tgttctattt caaccgcaac atccttagcc gtatagttag 3900
atggcctttc atgagaaata tatgtcacta atcgttgcaa cggtctcatt ccgtcatgag 3960
atccaccaac tcgaaatatg ttattcattc ctgcttctac aatcctttcc gcacctttta 4020
atgctaacgc atctcgatat ttaaatgatg actcccaagg aaaaatagat atggtttgcg 4080
tcttattttt ttgaacataa ggcaatattt gctcaatatt atcgacgtga tgaaggtaca 4140
cacatctgcc aagtggttga ttaaattcca cacctgcatt tgactcaata atcatccaac 4200
gttgatgaat atccacctct acttttaatc cagcaaacaa gctttctttt tgaactaaag 4260
aataggccgc cttttcatca aaatcttttt tggcattcgg taatatatgc gcatatagat 4320
taagtttttc tatcaacgct aacttaaatt cctcataatg atttcccatg taatatatgt 4380
tttgggcaga aaaacaagct cgctgatcgt aaaaacaaac atcatgagcc gcacctgtcg 4440
ctgcggacgt caaatcaaca ggattatcga taatgcaaag actcttttta gaaccaaatt 4500
taatcacatc agcataagat ggcgcatgct ctaccgccca attaatcgca tctggccctc 4560
cccaagcgac aataacatcc gcatgtcgca taatttcttt tgcgagtgat gtatcacctt 4620
ggtggggcca atatataaca gataaagagc gcgttatcgg atgattaggg tctacatcaa 4680
taaaacttaa cgctaatgca ttagcggtaa aaggatcggt tgacgatgtt tttataatac 4740
actgattctt agttaaaatt gcgcgtaata tagacatgat cccagataat ggaacattac 4800
ctgccaacag atgtacagat ttacctttcg gaaaagcccg aacataactt tcatcctgag 4860
gtagccattc atccatgata tggcgagaac caagttcatt ttctacaaca tcataaaggc 4920
cgcctttaga acataaaatc atagatatcc aattggcctc tagcttagcc atttcttctg 4980
aatatcccat atattttttt aagtcacgaa tgtatgtcct gcgtcttgag tattcttcat 5040
ttttccatct ttgccctacc gtatagagaa aattgacaat gttatgcaac cgtaattcgt 5100
tatttccatt acaatcaata atgtttttta catgagagtc attcaatatt ggcaggtaaa 5160
cactattatc accaaaatta atggattgca ctaaatcatc actttcggga aagatttcaa 5220
cctggccgtt aataatgaat gaaatttttt tagtcatatt tgccatcctc ctcgacttag 5280
gtatattcca tgtggtactt cttaatatta tcatcaacaa tattgattac atttttttgg 5340
ctcatcaaat cattcattgg ttcaaaggac agcaatacac ttttcgcacc acacttttca 5400
attgccaact tagccgcagt tatacactcc gtataatttc cgacagcgtt ttctgcaatt 5460
atttcttcaa gtttattttc gaaattttca ttagggtgca tttcaagaac ataatcacta 5520
ataaatgcac gcgtctcttg tttagcttta ttactatctt cgttatagtt aactaatatc 5580
attaactgat ggtctatctc tgataggtca acgtcatatt tatccgcaac ggctttatat 5640
ctttcagcat attcatatct aacatcatta gaatcatccc acttaaagat gagaggaata 5700
ccttttttgg ccgcccactc aacaatatga tgactggttg ctgttacata tttccgaggt 5760
ccgcctggcg tataagcatg gggatttaca gatattttag ggaagctata aaaatcgtta 5820
tctggattac aatagcctgt tgttaaagca tcgttaatga tttcataaca ctcttcaaat 5880
agttgctgtt gatattcaac cgggcgatta aaaaaatgca tttcatcttt tttttcgcaa 5940
tcactaaacc ctaaaataaa tctcccttca cttaactgat ccaataagca agcttcctcc 6000
gctatggcga caggatgatg agttgtaatg atgtgattta atgaaccaat tttaattttc 6060

-continued

```
tctgttaaac cgagcagaaa accagaaaca gtcagaggag cgccgacaac accattatct   6120
gaaaaatgat tttcatacac taaaatctgt tcaaaattca acttatcaac atactccgtt   6180
atttcctgca tgcgaactat actttgttct tgaacagttg ttgaattgat gaagttaagg   6240
aagaacaatc caaatttcat ttctttctcc tcctcgactt aatataatag cgaacgttgt   6300
ttttctttaa gaaatggcat gacatcagac tggaagagct tcatggaagc aataatttcg   6360
tctactgttc cattagcttc aaatccacaa caaatatttg atattcctgt agcatcaatg   6420
tctttttgaa ttatgtcaat acattcctgc ggcgttccca cgggattgat ttcgtaactg   6480
taatcaatac ggcgattagt atctttatgt ccttttaata caaagtcacg ccactgccct   6540
ttattgaaat cataacctct tgtttggtct gaatcatcaa aaatagtcgt agcattcaca   6600
taagaatcat accaatgccc cagaaatttc cggcaaatct ctttcgcttt aattgagtca   6660
tgatctacag atgttatata tgataagcaa tggtcgatat tatgaatatc gtgcccatat   6720
tcttgagcca cttcattata aagctcaagt tgtgctttct tttcgttagt atttataatc   6780
caacttaata tcatcggtag gccaaattga gcagcccact cagtcgtcga agctgattca   6840
gccaccacat aaaccggtgc gccacctctg ctatacgccg cggggtttac ttttacctta   6900
tggaacttga tatgttcatt atcagcttcc atatatccct ctgtcatgcc attctttatc   6960
agcccgtacc agcattccgc taaggcgcga ctgttattca tatctgtgcc gaatacgcga   7020
aagtccttgt tgtaaagccc tcggcaaata ccaaaccgaa atcgtccttt tgacatttga   7080
tccaataaat tcacatcttc aagttggcgt actggatggg ctgtgggaag aacaatagcg   7140
gcagttccta cattcaattt tttagtcgcg ccaagtaaat atgcagcagc gacataaggg   7200
ttaccaagca aaccaaactc cgtgaaatga tgctccagta accatacggt atcaaaacca   7260
cactcctcag agatgcgacc taatttaacc aaacgtttca ttacctctgt ttgagaaaat   7320
tggggaggtt ggtatgtaag caaaaagttt ccaaatttca tagagagtcc tcctcttgct   7380
tcatctgcag gatccactag atcattttac acaggagtct ggacttgact agacccctcg   7440
acctgcaggc atgcaagctt ggcgtaatca tggtcatagc tgtttcgcgg ccgcatcacg   7500
ccgctagagc ttgggctgca ggtcgacgga tccggtgcgg cttgctggag cgatcctgca   7560
tcccaaactc accctcttcc cggtagcggc ctgcccattt ccgggcagtg atcggggaga   7620
ccatgaacat ctttgcggcg atcgtggccg gatagccgtc ttcgacaatc agccgagcta   7680
accggagacg ggcacgagga gtgagaagag cgttcggatg ggtcatcaat tggcctccgc   7740
cgcggtcttc gtaagcgcgc gtctggtgag aagcatgatg acgagagcga tcgctgtcag   7800
caccgaagcg acccaaaccg gcgcgagcag ccccagcccg gtcgcgagcc cgagcgcacc   7860
aagcacgggc cccgctgcag ctccgatatt caatgctgcg gttgcgtacg aaccgcccat   7920
cgttggcgca cccgatgctg catacagcac acgcgtgatc agagtactgc cgacgccgaa   7980
cgacaggaat ccctgaacga ggacgaggac gataagcgca acgggatgag atgcgaccac   8040
tgccaacacg atccagcctg tcagcaatag cggtccgccg actgcgagca cgaggccagg   8100
tcgttgatct gatagtcgtc ctgcgatcgt gacgccaagg aacgatccga tgccgaacat   8160
caccagcgcg acggacaccc acgcttcggc caagcccgcg gtctcggtca cgatgggtgc   8220
caggaaggtg aatgccgcaa aggtccctcc gttgatcagc gctccgagtg ccatggccag   8280
gatgagccgc ggcgtcgcca actggctgag ctcgacacgg agccttggtg aggtcgcgct   8340
agtctcgctc cgaccaacat tgttcgtgac gccacgaatg actccaacgg ccgcgggaat   8400
acagaggatg gcgatcgccc agaacgtcgt tcgccagccc agcgctgtgc cgagcagtgc   8460
```

```
cccggcgggg acgcccacga cggttgcgat cgtcgtgccg gagagcagga tcgacagtgc   8520
acgccccttc tggttcgctg gcacgagggt agtggccgtg ctcagtgcta cggcgaggaa   8580
tcctgcgttt gcgagagcgc tgagcacccg ggtgatgagc aggagagaga acactggtgt   8640
catcgctccg atgacgtggc ttcccgcgaa cacgagaagg caaacgatca atgtgagccg   8700
cggtggccaa cggcgagcga atgccgccat cactggcgcg ccgacgacca taccgactgc   8760
gaatgcggag gtcagcaggc ccgcagtgcc gaccgagacg tcaagttcgg tcgcgatcgc   8820
ggggagcaat cccgcgagca tgaattctga agtgcccatg acgaagaccg ccagggcaag   8880
catgtagagg gcaaaaggca tcgagtactc cgaggtgtga gatcaagaaa tggttcttct   8940
tgtcaccacg gccagcgccc cgggtacgcc agacatacgc ccacacagat cgtgggcgtc   9000
gtaactagtg gttcaagggg ctggcggtgt gaccgacaac ccctgacctg tctgattcgg   9060
gactcgacat gccccaaact ctaacatgcc ttcaaggcgg aatcaagcgg tggatgcgcc   9120
acgcttgaat agttcgttaa gtatttcacg tggggttgcg ccgccgagga tttgtcgggg   9180
tgtttcgttg agctcatttt gcacccacgc gacatgttcg ggtgtgacgg tggcaaagtc   9240
ggtgcccttt ttgtagaacc tgcgcctgat ctcgccgttg gtgttctcgt tggttggtct   9300
ctgccacggt gagtgcggtt cacagaaaaa cacctggcag ccgtctttaa tctggacttg   9360
tgctgtgaca gccatttctg cgccttggtc ccatgtgatg gtctttagct gctcggtgtt   9420
gaggtctttg accatgtcct gcaggtcgac ctgcagccca agctctagcc ctcggcgctg   9480
catgcagttg cgcccactac accctcaatt ctgaagagcc atggtaccgg aattcactgg   9540
ccgtcgtttt acaacgtcgt gactgggaaa accctggcgt tacccaactt aatcgccttg   9600
cagcacatcc ccctttcgcc agctggcgta atagcgaaga ggcccgcacc gatcgccctt   9660
cccaacagtt gcgcagcctg aatggcgaat ggcgcctgat gcggtatttt ctccttacgc   9720
atctgtgcgg tatttcacac cgcatatggt gcactctcag tacaatctgc tctgatgccg   9780
catagttaag ccagccccga cacccgccaa cacccgctga cgcgccctga cgggcttgtc   9840
tgctcccggc atccgcttac agacaagctg tgaccgtctc cgggagctgc atgtgtcaga   9900
ggttttcacc gtcatcaccg aaacgcgcga gacgaaaggg cctcgtgata cgcctatttt   9960
tataggttaa tgtcatgata ataatggttt cttagacgtc aggtggcact tttcggggaa  10020
atgtgcgcgg aacccctatt tgtttatttt tctaaataca ttcaaatatg tatccgctca  10080
tgagacaata accctgataa atgcttcaat aatattgaaa aaggaagagt atgagtattc  10140
aacatttccg tgtcgccctt attccctttt ttgcggcatt ttgccttcct gtttttgctc  10200
acccagaaac gctggtgaaa gtaaaagatg ctgaagatca gttgggtgca cgagtgggtt  10260
acatcgaact ggatctcaac agcggtaaga tccttgagag ttttcgcccc gaagaacgtt  10320
ttccaatgat gagcactttt aaagttctgc tatgtggcgc ggtattatcc cgtattgacg  10380
ccgggcaaga gcaactcggt cgccgcatac actattctca gaatgacttg gttgagtact  10440
caccagtcac agaaaagcat cttacggatg gcatgacagt aagagaatta tgcagtgctg  10500
ccataaccat gagtgataac actgcggcca acttacttct gacaacgatc ggaggaccga  10560
aggagctaac cgcttttttg cacaacatgg gggatcatgt aactcgcctt gatcgttggg  10620
aaccggagct gaatgaagcc ataccaaacg acgagcgtga caccacgatg cctgtagcaa  10680
tggcaacaac gttgcgcaaa ctattaactg gcgaactact tactctagct tcccggcaac  10740
aattaataga ctggatggag gcggataaag ttgcaggacc acttctgcgc tcggcccttc  10800
cggctggctg gtttattgct gataaatctg gagccggtga gcgtgggtct cgcggtatca  10860
```

ttgcagcact ggggccagat ggtaagccct cccgtatcgt agttatctac acgacgggga 10920
gtcaggcaac tatggatgaa cgaaatagac agatcgctga gataggtgcc tcactgatta 10980
agcattggta actgtcagac caagtttact catatatact ttagattgat ttaaaacttc 11040
atttttaatt taaaaggatc taggtgaaga tcctttttga taatctcatg accaaaatcc 11100
cttaacgtga gttttcgttc cactgagcgt cagaccccgt agaaaagatc aaaggatctt 11160
cttgagatcc tttttttctg cgcgtaatct gctgcttgca aacaaaaaaa ccaccgctac 11220
cagcggtggt ttgtttgccg gatcaagagc taccaactct ttttccgaag gtaactggct 11280
tcagcagagc gcagatacca aatactgtcc ttctagtgta gccgtagtta ggccaccact 11340
tcaagaactc tgtagcaccg cctacatacc tcgctctgct aatcctgtta ccagtggctg 11400
ctgccagtgg cgataagtcg tgtcttaccg ggttggactc aagacgatag ttaccggata 11460
aggcgcagcg gtcgggctga acggggggtt cgtgcacaca gcccagcttg gagcgaacga 11520
cctacaccga actgagatac ctacagcgtg agctatgaga aagcgccacg cttcccgaag 11580
ggagaaaggc ggacaggtat ccggtaagcg gcagggtcgg aacaggagag cgcacgaggg 11640
agcttccagg gggaaacgcc tggtatcttt atagtcctgt cgggtttcgc cacctctgac 11700
ttgagcgtcg atttttgtga tgctcgtcag gggggcggag cctatggaaa aacgccagca 11760
acgcggcctt tttacggttc ctggcctttt gctggccttt tgctcacatg ttctttcctg 11820
cgttatcccc tgattctgtg gataaccgta ttaccgcctt tgagtgagct gataccgctc 11880
gccgcagccg aacgaccgag cgcagcgagt cagtgagcga ggaagcggaa gagcgcccaa 11940
tacgcaaacc gcctctcccc gcgcgttggc cgattcatta atgcagctgg cacgacaggt 12000
ttcccgactg gaaagcgggc agtgagcgca acgcaattaa tgtgagttag ctcactcatt 12060
aggcacccca ggctttacac tttatgcttc cggctcgtat gttgtgtgga attgtgagcg 12120
gataacaatt tcacacagga aacagctatg accatgatta cgccaagctt gggctgcagg 12180
tcgactctag aggatcccc 12199

<210> SEQ ID NO 2
<211> LENGTH: 5700
<212> TYPE: DNA
<213> ORGANISM: Artificial Sequence
<220> FEATURE:
<223> OTHER INFORMATION: Lux Operon

<400> SEQUENCE: 2
aaaatgatct agtggatcct gcagatgaag caagaggagg actctctatg aaatttggaa 60
actttttgct tacataccaa cctccccaat tttctcaaac agaggtaatg aaacgtttgg 120
ttaaattagg tcgcatctct gaggagtgtg gttttgatac cgtatggtta ctggagcatc 180
atttcacgga gtttggtttg cttggtaacc cttatgtcgc tgctgcatat ttacttggcg 240
cgactaaaaa attgaatgta ggaactgccg ctattgttct tcccacagcc catccagtac 300
gccaacttga agatgtgaat ttattggatc aaatgtcaaa aggacgattt cggtttggta 360
tttgccgagg gctttacaac aaggactttc gcgtattcgg cacagatatg aataacagtc 420 gcgcccttagc ggaatgctgg tacgggctga taaagaatgg catgacagag ggatatatgg 480
aagctgataa tgaacatatc aagttccata aggtaaaagt aaaccccgcg gcgtatagca 540
gaggtggcgc accggtttat gtggtggctg aatcagcttc gacgactgag tgggctgctc 600
aatttggcct accgatgata ttaagttgga ttataaatac taacgaaaag aaagcacaac 660
ttgagcttta taatgaagtg gctcaagaat atgggcacga tattcataat atcgaccatt 720

-continued

```
gcttatcata tataacatct gtagatcatg actcaattaa agcgaaagag atttgccgga    780
aatttctggg gcattggtat gattcttatg tgaatgctac gactattttt gatgattcag    840
accaaacaag aggttatgat ttcaataaag ggcagtggcg tgactttgta ttaaaaggac    900
ataaagatac taatcgccgt attgattaca gttacgaaat caatcccgtg ggaacgccgc    960
aggaatgtat tgacataatt caaaaagaca ttgatgctac aggaatatca aatatttgtt   1020
gtggatttga agctaatgga acagtagacg aaattattgc ttccatgaag ctcttccagt   1080
ctgatgtcat gccatttctt aaagaaaaac aacgttcgct attatattaa gtcgaggagg   1140
agaaagaaat gaaatttgga ttgttcttcc ttaacttcat caattcaaca actgttcaag   1200
aacaaagtat agttcgcatg caggaaataa cggagtatgt tgataagttg aattttgaac   1260
agattttagt gtatgaaaat catttttcag ataatggtgt tgtcggcgct cctctgactg   1320
tttctggttt tctgctcggt ttaacagaga aaattaaaat tggttcatta aatcacatca   1380
ttacaactca tcatcctgtc gccatagcgg aggaagcttg cttattggat cagttaagtg   1440
aagggagatt tattttaggg tttagtgatt gcgaaaaaaa agatgaaatg cattttttta   1500
atcgcccggt tgaatatcaa cagcaactat ttgaagagtg ttatgaaatc attaacgatg   1560
ctttaacaac aggctattgt aatccagata acgattttta tagcttccct aaaatatctg   1620
taaatcccca tgcttatacg ccaggcggac ctcggaaata tgtaacagca accagtcatc   1680
atattgttga gtgggcggcc aaaaaaggta ttcctctcat ctttaagtgg gatgattcta   1740
atgatgttag atatgaatat gctgaaagat ataaagccgt tgcggataaa tatgacgttg   1800
acctatcaga gatagaccat cagttaatga tattagttaa ctataacgaa gatagtaata   1860
aagctaaaca agagacgcgt gcatttatta gtgattatgt tcttgaaatg caccctaatg   1920
aaaatttcga aaataaactt gaagaaataa ttgcagaaaa cgctgtcgga aattatacgg   1980
agtgtataac tgcggctaag ttggcaattg aaaagtgtgg tgcgaaaagt gtattgctgt   2040
cctttgaacc aatgaatgat ttgatgagcc aaaaaaatgt aatcaatatt gttgatgata   2100
atattaagaa gtaccacatg gaatatacct aagtcgagga ggatggcaaa tatgactaaa   2160
aaaatttcat tcattattaa cggccaggtt gaaatctttc ccgaaagtga tgatttagtg   2220
caatccatta attttggtga taatagtgtt tacctgccaa tattgaatga ctctcatgta   2280
aaaaacatta ttgattgtaa tggaaataac gaattacggt tgcataacat tgtcaatttt   2340
ctctatacgg tagggcaaag atggaaaaat gaagaatact caagacgcag gacatacatt   2400
cgtgacttaa aaaaatatat gggatattca gaagaaatgg ctaagctaga ggccaattgg   2460
atatctatga ttttatgttc taaaggcggc ctttatgatg ttgtagaaaa tgaacttggt   2520
tctcgccata tcatggatga atggctacct caggatgaaa gttatgttcg ggcttttccg   2580
aaaggtaaat ctgtacatct gttggcaggt aatgttccat tatctgggat catgtctata   2640
ttacgcgcaa ttttaactaa gaatcagtgt attataaaaa catcgtcaac cgatcctttt   2700
accgctaatg cattagcgtt aagttttatt gatgtagacc ctaatcatcc gataacgcgc   2760
tctttatctg ttatatattg gccccaccaa ggtgatacat cactcgcaaa agaaattatg   2820
cgacatgcgg atgttattgt cgcttgggga gggccagatg cgattaattg ggcggtagag   2880
catgcgccat cttatgctga tgtgattaaa tttggttcta aaaagagtct ttgcattatc   2940
gataatcctg ttgatttgac gtccgcagcg acaggtgcgg ctcatgatgt ttgtttttac   3000
gatcagcgag cttgtttttc tgcccaaaac atatattaca tgggaaatca ttatgaggaa   3060
tttaagttag cgttgataga aaaacttaat ctatatgcgc atatattacc gaatgccaaa   3120
```

-continued

```
aaagattttg atgaaaaggc ggcctattct ttagttcaaa aagaaagctt gtttgctgga   3180
ttaaaagtag aggtggatat tcatcaacgt tggatgatta ttgagtcaaa tgcaggtgtg   3240
gaatttaatc aaccacttgg cagatgtgtg taccttcatc acgtcgataa tattgagcaa   3300
atattgcctt atgttcaaaa aaataagacg caaaccatat ctatttttcc ttgggagtca   3360
tcatttaaat atcgagatgc gttagcatta aaaggtgcgg aaaggattgt agaagcagga   3420
atgaataaca tatttcgagt tggtggatct catgacggaa tgagaccgtt gcaacgatta   3480
gtgacatata tttctcatga aaggccatct aactatacgg ctaaggatgt tgcggttgaa   3540
atagaacaga ctcgattcct ggaagaagat aagttccttg tatttgtccc ataagtcgag   3600
gaggagtaaa agtatggaaa atgaatcaaa atataaaacc atcgaccacg ttatttgtgt   3660
tgaaggaaat aaaaaaattc atgtttggga aacgctgcca gaagaaaaca gcccaaagag   3720
aaagaatgcc attattattg cgtctggttt tgcccgcagg atggatcatt ttgctggtct   3780
ggcggaatat ttatcgcgga atggatttca tgtgatccgc tatgattcgc ttcaccacgt   3840
tggattgagt tcagggacaa ttgatgaatt tacaatgtct ataggaaagc agagcttgtt   3900
agcagtggtt gattggttaa ctacacgaaa aataaataac ttcggtatgt tggcttcaag   3960
cttatctgcg cggatagctt atgcaagcct atctgaaatc aatgcttcgt ttttaatcac   4020
cgcagtcggt gttgttaact taagatattc tcttgaaaga gctttagggt ttgattatct   4080
cagtctaccc attaatgaat tgccggataa tctagatttt gaaggccata aattgggtgc   4140
tgaagtcttt gcgagagatt gtcttgattt tggttgggaa gatttagctt ctacaattaa   4200
taacatgatg tatcttgata taccgtttat tgcttttact gcaaataacg ataattgggt   4260
caagcaagat gaagttatca cattgttatc aaatattcgt agtaatcgat gcaagatata   4320
ttctttgtta ggaagttcgc atgacttgag tgaaaattta gtggtcctgc gcaattttta   4380
tcaatcggtt acgaaagccg ctatcgcgat ggataatgat catctggata ttgatgttga   4440
tattactgaa ccgtcatttg aacatttaac tattgcgaca gtcaatgaac gccgaatgag   4500
aattgagatt gaaaatcaag caatttctct gtcttaagtc gaggaggaaa acaggtatga   4560
cttcatatgt tgataaacaa gaaattacag caagctcaga aattgatgat ttgatttttt   4620
cgagcgatcc attagtgtgg tcttacgacg agcaggaaaa aatcagaaag aaacttgtgc   4680
ttgatgcatt tcgtaatcat tataaacatt gtcgagaata tcgtcactac tgtcaggcac   4740
acaaagtaga tgacaatatt acggaaattg atgacatacc tgtattccca acatcggttt   4800
ttaagtttac tcgcttatta acttctcagg aaaacgagat tgaaagttgg tttaccagta   4860
gcggcacgaa tggtttaaaa agtcaggtgg cgcgtgacag attaagtatt gagagactct   4920
taggctctgt gagttatggc atgaaatatg ttggtagttg gtttgatcat caaatagaat   4980
tagtcaattt gggaccagat agatttaatg ctcataatat ttggtttaaa tatgttatga   5040
gtttggtgga attgttatat cctacgacat ttaccgtaac agaagaacga atagattttg   5100
ttaaaacatt gaatagtctt gaacgaataa aaaatcaagg gaaagatctt tgtcttattg   5160
gttcgccata ctttatttat ttactctgcc attatatgaa agataaaaaa atctcatttt   5220
ctggagataa aagcctttat atcataaccg gaggcggctg gaaaagttac gaaaaagaat   5280
ctctgaaacg tgatgatttc aatcatcttt tatttgatac tttcaatctc agtgatatta   5340
gtcagatccg agatatattt aatcaagttg aactcaacac ttgtttcttt gaggatgaaa   5400
tgcagcgtaa acatgttccg ccgtgggtat atgcgcgagc gcttgatcct gaaacgttga   5460
aacctgtacc tgatggaacg ccggggttga tgagttatat ggatgcgtca gcaaccagtt   5520
```

-continued

```
atccagcatt tattgttacc gatgatgtcg ggataattag cagagaatat ggtaagtatc   5580

ccggcgtgct cgttgaaatt ttacgtcgcg tcaatacgag gacgcagaaa gggtgtgctt   5640

taagcttaac cgaagcgttt gatagttaag tcgaggaggg aaataataaa tggctaaaat   5700
```

```
<210> SEQ ID NO 3
<211> LENGTH: 18357
<212> TYPE: DNA
<213> ORGANISM: Artificial Sequence
<220> FEATURE:
<223> OTHER INFORMATION: Plasmid

<400> SEQUENCE: 3

caactgcctg gcacaataat tttccttttt tcagttacaa caagctccaa tacgcaaacc     60

gcctctcccc gcgcgttggc cgattcatta atgcagctgg cacgacaggt ttcccgactg    120

gaaagcgggc agtgagcgca acgcaattaa tgtgagttag ctcactcatt aggcacccca    180

ggctttacac tttatgcttc cggctcgtat gttgtgtgga attgtgagcg gataacaatt    240

tcacacagga aacagctatg accatgatta cgccaagctt gcatgcctgc aggtcgaggg    300

gtctagtcaa gtccagactc ctgtgtaaaa tgatctagtg gatcctgcag atgaagcaag    360

aggaggactc tctatgaaat ttggaaactt tttgcttaca taccaacctc cccaattttc    420

tcaaacagag gtaatgaaac gtttggttaa attaggtcgc atctctgagg agtgtggttt    480

tgataccgta tggttactgg agcatcattt cacggagttt ggtttgcttg gtaaccctta    540

tgtcgctgct gcatatttac ttggcgcgac taaaaaattg aatgtaggaa ctgccgctat    600

tgttcttccc acagcccatc cagtacgcca acttgaagat gtgaatttat tggatcaaat    660

gtcaaaagga cgatttcggt ttggtatttg ccgagggctt tacaacaagg actttcgcgt    720

attcggcaca gatatgaata acagtcgcgc cttagcggaa tgctggtacg ggctgataaa    780

gaatggcatg acagagggat atatggaagc tgataatgaa catatcaagt tccataaggt    840

aaaagtaaac cccgcggcgt atagcagagg tggcgcaccg gtttatgtgg tggctgaatc    900

agcttcgacg actgagtggg ctgctcaatt tggcctaccg atgatattaa gttggattat    960

aaatactaac gaaaagaaag cacaacttga gctttataat gaagtggctc aagaatatgg   1020

gcacgatatt cataatatcg accattgctt atcatatata acatctgtag atcatgactc   1080

aattaaagcg aaagagattt gccggaaatt tctggggcat tggtatgatt cttatgtgaa   1140

tgctacgact atttttgatg attcagacca aacaagaggt tatgatttca ataaagggca   1200

gtggcgtgac tttgtattaa aaggacataa agatactaat cgccgtattg attacagtta   1260

cgaaatcaat cccgtgggaa cgccgcagga atgtattgac ataattcaaa aagacattga   1320

tgctacagga atatcaaata tttgttgtgg atttgaagct aatggaacag tagacgaaat   1380

tattgcttcc atgaagctct tccagtctga tgtcatgcca tttcttaaag aaaaacaacg   1440

ttcgctatta tattaagtcg aggaggagaa agaaatgaaa tttggattgt tcttccttaa   1500

cttcatcaat tcaacaactg ttcaagaaca aagtatagtt cgcatgcagg aaataacgga   1560

gtatgttgat aagttgaatt ttgaacagat tttagtgtat gaaaatcatt tttcagataa   1620

tggtgttgtc ggcgctcctc tgactgtttc tggttttctg ctcggtttaa cagagaaaat   1680

taaaattggt tcattaaatc acatcattac aactcatcat cctgtcgcca tagcggagga   1740

agcttgctta ttggatcagt taagtgaagg gagatttatt ttagggttta gtgattgcga   1800

aaaaaaagat gaaatgcatt tttttaatcg cccggttgaa tatcaacagc aactatttga   1860

agagtgttat gaaatcatta acgatgcttt aacaacaggc tattgtaatc cagataacga   1920
```

-continued

```
tttttatagc ttccctaaaa tatctgtaaa tccccatgct tatacgccag gcggacctcg   1980
gaaatatgta acagcaacca gtcatcatat tgttgagtgg gcggccaaaa aaggtattcc   2040
tctcatcttt aagtgggatg attctaatga tgttagatat gaatatgctg aaagatataa   2100
agccgttgcg gataaatatg acgttgacct atcagagata gaccatcagt taatgatatt   2160
agttaactat aacgaagata gtaataaagc taaacaagag acgcgtgcat ttattagtga   2220
ttatgttctt gaaatgcacc ctaatgaaaa tttcgaaaat aaacttgaag aaataattgc   2280
agaaaacgct gtcggaaatt atacggagtg tataactgcg gctaagttgg caattgaaaa   2340
gtgtggtgcg aaaagtgtat tgctgtcctt tgaaccaatg aatgatttga tgagccaaaa   2400
aaatgtaatc aatattgttg atgataatat taagaagtac cacatggaat atacctaagt   2460
cgaggaggat ggcaaatatg actaaaaaaa tttcattcat tattaacggc caggttgaaa   2520
tctttcccga aagtgatgat ttagtgcaat ccattaattt tggtgataat agtgtttacc   2580
tgccaatatt gaatgactct catgtaaaaa acattattga ttgtaatgga aataacgaat   2640
tacggttgca taacattgtc aattttctct atacggtagg gcaaagatgg aaaaatgaag   2700
aatactcaag acgcaggaca tacattcgtg acttaaaaaa atatatggga tattcagaag   2760
aaatggctaa gctagaggcc aattggatat ctatgatttt atgttctaaa ggcggccttt   2820
atgatgttgt agaaaatgaa cttggttctc gccatatcat ggatgaatgg ctacctcagg   2880
atgaaagtta tgttcgggct tttccgaaag gtaaatctgt acatctgttg gcaggtaatg   2940
ttccattatc tgggatcatg tctatattac gcgcaatttt aactaagaat cagtgtatta   3000
taaaaacatc gtcaaccgat ccttttaccg ctaatgcatt agcgttaagt tttattgatg   3060
tagaccctaa tcatccgata acgcgctctt tatctgttat atattggccc caccaaggtg   3120
atacatcact cgcaaaagaa attatgcgac atgcggatgt tattgtcgct tggggagggc   3180
cagatgcgat taattgggcg gtagagcatg cgccatctta tgctgatgtg attaaatttg   3240
gttctaaaaa gagtctttgc attatcgata atcctgttga tttgacgtcc gcagcgacag   3300
gtgcggctca tgatgtttgt ttttacgatc agcgagcttg tttttctgcc caaaacatat   3360
attacatggg aaatcattat gaggaattta agttagcgtt gatagaaaaa cttaatctat   3420
atgcgcatat attaccgaat gccaaaaaag attttgatga aaaggcggcc tattctttag   3480
ttcaaaaaga aagcttgttt gctggattaa aagtagaggt ggatattcat caacgttgga   3540
tgattattga gtcaaatgca ggtgtggaat ttaatcaacc acttggcaga tgtgtgtacc   3600
ttcatcacgt cgataatatt gagcaaatat tgccttatgt tcaaaaaaat aagacgcaaa   3660
ccatatctat ttttccttgg gagtcatcat ttaaatatcg agatgcgtta gcattaaaag   3720
gtgcggaaag gattgtagaa gcaggaatga ataacatatt tcgagttggt ggatctcatg   3780
acggaatgag accgttgcaa cgattagtga catatatttc tcatgaaagg ccatctaact   3840
atacggctaa ggatgttgcg gttgaaatag aacagactcg attcctggaa gaagataagt   3900
tccttgtatt tgtcccataa gtcgaggagg agtaaaagta tggaaaatga atcaaaatat   3960
aaaaccatcg accacgttat ttgtgttgaa ggaaataaaa aaattcatgt ttgggaaacg   4020
ctgccagaag aaaacagccc aaagagaaag aatgccatta ttattgcgtc tggttttgcc   4080
cgcaggatgg atcattttgc tggtctggcg gaatatttat cgcggaatgg atttcatgtg   4140
atccgctatg attcgcttca ccacgttgga ttgagttcag ggacaattga tgaatttaca   4200
atgtctatag gaaagcagag cttgttagca gtggttgatt ggttaactac acgaaaaata   4260
aataacttcg gtatgttggc ttcaagctta tctgcgcgga tagcttatgc aagcctatct   4320
```

-continued gaaatcaatg cttcgttttt aatcaccgca gtcggtgttg ttaacttaag atattctctt 4380
gaaagagctt tagggtttga ttatctcagt ctacccatta atgaattgcc ggataatcta 4440
gattttgaag gccataaatt gggtgctgaa gtctttgcga gagattgtct tgattttggt 4500
tgggaagatt tagcttctac aattaataac atgatgtatc ttgatatacc gtttattgct 4560
tttactgcaa ataacgataa ttgggtcaag caagatgaag ttatcacatt gttatcaaat 4620
attcgtagta atcgatgcaa gatatattct ttgttaggaa gttcgcatga cttgagtgaa 4680
aatttagtgg tcctgcgcaa tttttatcaa tcggttacga aagccgctat cgcgatggat 4740
aatgatcatc tggatattga tgttgatatt actgaaccgt catttgaaca tttaactatt 4800
gcgacagtca atgaacgccg aatgagaatt gagattgaaa atcaagcaat ttctctgtct 4860
taagtcgagg aggaaaacag gtatgacttc atatgttgat aaacaagaaa ttacagcaag 4920
ctcagaaatt gatgatttga tttttcgag cgatccatta gtgtggtctt acgacgagca 4980
ggaaaaaatc agaaagaaac ttgtgcttga tgcatttcgt aatcattata aacattgtcg 5040
agaatatcgt cactactgtc aggcacacaa agtagatgac aatattacgg aaattgatga 5100
catacctgta ttcccaacat cggtttttaa gtttactcgc ttattaactt ctcaggaaaa 5160
cgagattgaa agttggttta ccagtagcgg cacgaatggt ttaaaaagtc aggtggcgcg 5220
tgacagatta agtattgaga gactcttagg ctctgtgagt tatggcatga aatatgttgg 5280
tagttggttt gatcatcaaa tagaattagt caatttggga ccagatagat ttaatgctca 5340
taatatttgg tttaaatatg ttatgagttt ggtggaattg ttatatccta cgacatttac 5400
cgtaacagaa gaacgaatag attttgttaa aacattgaat agtcttgaac gaataaaaaa 5460
tcaagggaaa gatctttgtc ttattggttc gccatacttt atttatttac tctgccatta 5520
tatgaaagat aaaaaaatct cattttctgg agataaaagc ctttatatca taaccggagg 5580
cggctggaaa agttacgaaa aagaatctct gaaacgtgat gatttcaatc atcttttatt 5640
tgatactttc aatctcagtg atattagtca gatccgagat atatttaatc aagttgaact 5700
caacacttgt ttctttgagg atgaaatgca gcgtaaacat gttccgccgt gggtatatgc 5760
gcgagcgctt gatcctgaaa cgttgaaacc tgtacctgat ggaacgccgg ggttgatgag 5820
ttatatggat gcgtcagcaa ccagttatcc agcatttatt gttaccgatg atgtcgggat 5880
aattagcaga gaatatggta agtatcccgg cgtgctcgtt gaaattttac gtcgcgtcaa 5940
tacgaggacg cagaaagggt gtgctttaag cttaaccgaa gcgtttgata gttaagtcga 6000
ggagggaaat aataaatggc taaaatgaga atatcaccgg aattgaaaaa actgatcgaa 6060
aaataccgct gcgtaaaaga tacggaagga atgtctcctg ctaaggtata taagctggtg 6120
ggagaaaatg aaaacctata tttaaaaatg acggacagcc ggtataaagg gaccacctat 6180
gatgtggaac gggaaaagga catgatgcta tggctggaag gaaagctgcc tgttccaaag 6240
gtcctgcact ttgaacggca tgatggctgg agcaatctgc tcatgagtga ggccgatggc 6300
gtcctttgct cggaagagta tgaagatgaa caaagccctg aaaagattat cgagctgtat 6360
gcggagtgca tcaggctctt tcactccatc gacatatcgg attgtcccta tacgaatagc 6420
ttagacagcc gcttagccga attggattac ttactgaata acgatctggc cgatgtggat 6480
tgcgaaaact gggaagaaga cactccattt aaagatccgc gcgagctgta tgattttta 6540
aagacggaaa agcccgaaga ggaacttgtc ttttcccacg gcgacctggg agacagcaac 6600
atctttgtga aagatggcaa agtaagtggc tttattgatc ttgggagaag cggcagggcg 6660
gacaagtggt atgacattgc cttctgcgtc cggtcgatca gggaggatat cggggaagaa 6720

-continued

```
cagtatgtcg agctattttt tgacttactg gggatcaagc ctgattggga gaaaataaaa   6780
tattatattt tactggatga attgttttag tacctagatt tagatgtcta aaaagcttta   6840
actacaagct ttttagacat ctaatctttt ctgaagtaca tccgcaactg tcgaatccaa   6900
tgtttttacc atttctactt atcaaaattg atgtattttc ttgaagaata aatccattca   6960
tcatgtaggt ccataagaac ggctccaatt aagcgattgg ctgatgtttg attggggaag   7020
atgcgaataa tcttttctct tctgcgtact tcttgattca gtcgttcaat tagattggta   7080
ctctttagtc gattgtggga atttccttgt acggtatatt gaaaggcgtc ttcgaatcca   7140
tcatccaatg atgcgcaagc ttttgaatat tttggttgat cgatataatc atgaatcaat   7200
cgatttttag cctcacgcgc taagttaata tctgtgaact taaaaattcc tttaacagct   7260
tctctgaaag attttgaatt ttttttagga atggtggtaa agatatttct taggaagtga   7320
acttggcatc tttgccaact tacgttggtg aaggattttc taatggcaga gactaatcct   7380
ttgtgcgcat cagaaataac gagttccgta ccttgtaaac cgcgttcttt taggtattca   7440
aaaaatgttg tccaggtctc ttcgctttcg ccactttgaa tcatgaagcc gataatttca   7500
cggtcgccat ctttggttat tccaatcgct atatgacagc tttttgagag tactcgattt   7560
tcttctcgta cttttatata gagtacatcg gtcattaagt aaggataatt tttttctgat   7620
aataaacgat tctgccactc gttaaccata ggttctagct gttctgttaa gctagaaacg   7680
aaggacttag agacggattt accacaaagt tcttccacaa tttttgatac tttacgagtt   7740
gaaacgcctg atacatacat ttccaacatt gaagccatga gggctttttc gtttcgttga   7800
taacgttcaa acactgtggg tgaaaaatgg ccatcacgtg ttctgggtac ttttaattct   7860
agcgtgccta cacgtgtcgt aaagctgcgc tcataatagc catttcgttg actttgtcgg   7920
ttttctgttc gttcatattc ttttgcttga atatattctg ttcgttgatt ttccattagt   7980
tgattaaata ccgttgttaa aatattttta gaaacgtcat cctttacaga atattcaata   8040
atgctttgaa tctcttcgct tttcagtgta aaatgtactt gggtcatgta aaagtcctcc   8100
tgggtatgtt tttgtcgtta aaaacattgt accgtaaaag gactgttata tggccttttt   8160
acttttacac aattatacgg actttatctc agaaagactt acgactcctg taatgatagc   8220
aacaacagct ccaattaaag ctgtaatacc aatatctaaa ccttttggtt gccaaatcac   8280
aaaggttaaa gttaaaagaa aaattacaat tgctaaaata gtcatcaaca gtcacctgat   8340
ttcacatttt tacatacaca tctttgatta gatgtattaa tgatgttcaa gttttggata   8400
atatcatcta aaatagcatg attaagttga taccaatgtt tattgccgtc ttttcgtgtt   8460
gtaactaatt cattatctac taatgacttc atatgatgac ttagtgtagg ttgtgagaat   8520
tgaaagtgtt ctaataagtc acaagcgcat agctcaccac aagaaagtaa atctaatatt   8580
tctaacctac ttgaatctga taaaattttt aatattgttg atagttcttt ataagacatg   8640
aataaacctc ctagatgtta aatagattaa catctatata gattattgtc tatgttattt   8700
tatttactat tttttattct atatatagtt tgacgtgtaa taccaacttc tttagctata   8760
gtacttatag atttaccctg ttcaagtaat tcaacaactc ggtaataaac taaacgcttt   8820
tgtgggtctt tagcattggg agaatacaga acaggtctcc ctttatatat accttttttct   8880
ttggcgactt gaatcccttg agcttgtcga cctgcaggca tgcaagcttg gcgtaatcat   8940
ggtcatagct gtttcctgag actctagagg atcccccatc gatggggtac cgagctcgaa   9000
ttcactggcc gtcgttttac aacgtcgtga ctgggaaaac cctggcgtta cccaacttaa   9060
tcgccttgca gcacatcccc ctttcgccag ctggcgtaat agcgaagagg cccgcaccga   9120
```

tcgcccttcc caacagttgc gcagcctgaa tggcgaatgc cgggaattat tcaccactcc 9180
aagaattgga gccaatcaat tcttgcggag aactgtgaat gcgcaaacca acccttggca 9240
gaacatatcc atcgcgtccg ccatctccag cagccgcacg cggcgcatct cggctgtttt 9300
ggcggatgag agaagatttt cagcctgata cagattaaat cagaacgcag aagcggtctg 9360
ataaaacaga atttgcctgg cggcagtagc gcggtggtcc cacctgaccc catgccgaac 9420
tcagaagtga aacgccgtag cgccgatggt agtgtggggt ctccccatgc gagagtaggg 9480
aactgccagg catcaaataa aacgaaaggc tcagtcgaaa gactgggcct ttcgttttat 9540
ctgttgtttg tcggtgaacg ctctcctgag taggacaaat ccgccgggag cggatttgaa 9600
cgttgcgaag caacggcccg gagggtggcg ggcaggacgc ccgccataaa ctgccaggca 9660
tcaaattaag cagaaggcca tcctgacgga tggccttttt gcgtttctac aaactcttcc 9720
tgtcgtcata tctacaagcc atccccccac agatacggta aactagcctc gtttttgcat 9780
caggaaagca gctgttttgg cggatgagag aagattttca gcctgataca gattaaatca 9840
gaacgcagaa gcggtctgat aaaacagaat ttgcctggcg gcagtagcgc ggtggtccca 9900
cctgacccca tgccgaactc agaagtgaaa cgccgtagcg ccgatggtag tgtggggtct 9960
ccccatgcga gagtagggaa ctgccaggca tcaaataaaa cgaaaggctc agtcgaaaga 10020
ctgggccttt cgttttatct gttgtttgtc ggtgaacgct ctcctgagta ggacaaatcc 10080
gccgggagcg gatttgaacg ttgcgaagca acggcccgga gggtggcggg caggacgccc 10140
gccataaact gccaggcatc aaattaagca gaaggccatc ctgacggatg gcctttttgc 10200
gtttctacaa actcttcctg tcgtcatatc tacaagccat ccccccacag atacggtaaa 10260
ctagcctcgt ttttgcatca ggaaagcagt cgggcagcgt tgggtcctgg ccacgggtgc 10320
gcatgatcgt gctcctgtcg ttgaggaccc ggctaggctg gcggggttgc cttactggtt 10380
agcagaatga ataattctat gctcctatat tgataagaat aaacttaata ctataaatga 10440
ggtgttaggg atttaattat tctttattga tataaaaagt cctagcaatc caaatgggat 10500
tgctaggacc aaacaaagta gattatatag cataaatagg tttaattttg ctacgggggc 10560
gttatttagg ttttttcttc tttcgaaaaa atctttcttt atgaagttaa aagctatgta 10620
ttcaatagca tattttgaat atggacatag aatagtgctt atcactattg catatagcat 10680
cttatctgac acaaggaaat aataccottc gctgtttttt gttataaggt atatatatat 10740
aagtgtgcag tacaggccaa ataaaatatt ttttatgtag tatcttaagc tcataaatta 10800
aacctcgcca tatattcttt tcattttata aggatcgagt tatgaggaaa agatttttg 10860
tgggaatatt cgcgataaac ctccttgttg gatgtcaggc taactatata cctgatgttc 10920
agggagggac catcgcacca tcctcctctt ctaaactgac ggggatcgcg gttcagtaga 10980
aaagattaaa ggatcttctt gagatccttt ttttctgcgc gtaatctgct gcttgcaaac 11040
aaaaaaacca ccgctaccaa cggtggtttg tttgccggat caagagctac caactctttt 11100
tccgaaggta actggcttca gcagagcgca gataccaaat actgtccttc tagtgtagcc 11160
gtagtcgggc cactacttca agaactctgt agcaccgttt gtgccatcat cgctctgcta 11220
atccggttac cagtggctgc tgccagtggc gttaaggcgt gccttaccgg gttggactca 11280
agacgatagt taccggataa ggcgcagcgg tcgggctgaa cggggggttc gtgcacacag 11340
cccagcttgg agcgaacgac ctacaccgaa ctgagatacc aacagcgtga gctatgagaa 11400
agcgccacgc ttcccgaagg gagaaaggcg gacaggtatc cggtaagcgg cagggtcgga 11460
acaggagagc gcacgaggga gcttccaggg ggaaacgcct ggtagcttta tagtcctgtc 11520

-continued gggtttcgcc acctctgact tgagcgtcta tttttgtgat gctcgtcagg ggggcggagc 11580
ctatggaaaa acgcctgcta cgtggccttc ttcctgttcc tggtcttttg ctcacatgtt 11640
ctttccggcc ttatcccctg attctgtgga taactgtgtt accgtttttg tgtgagtcag 11700
taccgctcgc cgcagtcgaa cgaccgagcg tagcgagtca gtgagcgagg aagcggaaaa 11760
gcgcctggac gtgcattttc tccttacgca tctgtgcggc atttcacacc cggcatggcg 11820
tacttttcat acaatccgca ctgatgccgc atggttaagc cagtatacac tccgctatcg 11880
ctacgtgact gggtcagggc tgcgccccga cacccgctaa aacctgctga cgcgccctga 11940
cgggcttgtc agctcccggc atccgctcac agacaagctg tgaccgtctc cgggagctgc 12000
atgtgtcaga ggttttcacc gtcatccccg aaacgtgcga ggcagctgcg gtaaagctca 12060
tcggcgtggt cgtgaagcga ttcacaaata tcggcctgtt catctgcgtc cagttcgttg 12120
agcttctcca gcagcgttaa tgtctggctt ctgataaagc gggccatgtt aagggcggtt 12180
ttttcctgtt tagtcactga tgcctccgtg taagggggat ttctgttcat ggggtaatga 12240
taccgatgaa acgcgagagg atgctcacaa tacgggttac tgatgatgaa catgcccggt 12300
tacttgaacg ctgtgagggt aaacaactgg cggtatggat gcggcgggtc tgcctggggg 12360
agccggttgc ccgttccgga aaactgccga cactggcacc gccgttactg cgtcagctgg 12420
ccgccatcgg aaataacctg aatcagacag cccgtaaggt gaacagcggg cagtggtctt 12480
ccggcgaccg ggttcaggtg gtggccgcac tgatggccat cggtagcttg cggtcgggat 12540
gagctgcgcc ggctgcgtct ggccgtcagg gaacaggggg cgcgggatga tagttaaatt 12600
tcatgcctcc aggcgctttt ccgcttcctc gctcactgac tcgctacgct cggtcgttcg 12660
actgcggcga gcggtactga ctcacacaaa aacggtaaca cagttatcca cagaatcagg 12720
ggataaggcc ggaaagaaca tgtgagcaaa agaccaggaa caggaagaag gccacgtagc 12780
aggcgttttt ccataggctc cgccccccctg acgagcatca caaaaataga cgctcaagtc 12840
agaggtggcg aaacccgaca ggactataaa gctaccaggc gtttccccct ggaagctccc 12900
tcgtgcgctc tcctgttccg accctgccgc ttaccggata cctgtccgcc tttctccctt 12960
cgggaagcgt ggctggggaa aaggtggtgg cagtggtccg gttgattacc tgctggggag 13020
ggagcgtaac cgggaaggtg caacggtact tcagggtaac ccggaagaag tcagagcctg 13080
agcaggaatc ccattccggc agaacgtttg attttgaaaa agagcctgac aagctgaacg 13140
cactggtcag tgatgccatg aaggatatac aggaagaaat cgatcttcag tcccttgtta 13200
accttttcca ttggaacagt ggactaaaag gcatgcaatt tcataatcaa agagagcgaa 13260
aaagtagaac gaatgatgat attgaccatg agcgaacacg tgaaaattat gatttgaaaa 13320
atgataaaaa tattgattac aacgaacgtg tcaaagaaat tattgaatca caaaaaacag 13380
gtacaagaaa aacgaggaaa gatgctgttc ttgtaaatga gttgctagta acatctgacc 13440
gagatttttt tgagcaactg gatcagtaca agaaagatac tgtatttcat aaacaggaac 13500
tgcaagaagt taaggatgag ttacagaagg caaataagca gttacagagt ggaatagagc 13560
atatgaggtc tacgaaaccc tttgattatg aaaatgagcg tacaggtttg ttctctggac 13620
gtgaagagac tggtagaaag atattaactg ctgatgaatt tgaacgcctg caagaaacaa 13680
tctcttctgc agaacggatt gttgatgatt acgaaaatat taagagcaca gactattaca 13740
cagaaaatca agaattaaaa aaacgtagag agagtttgaa agaagtagtg aatacatgga 13800
aagaggggta tcacgaaaaa agtaaagagg ttaataaatt aaagcgagag aatgatagtt 13860
tgaatgagca gttgaatgta tcagagaaat ttcaagctag tacagtgact ttatatcgtg 13920

```
ctgcgagggc gaatttccct gggtttgaga aagggtttaa taggcttaaa gagaaattct  13980
ttaatgattc caaatttgag cgtgtgggac agtttatgga tgttgtacag gataatgtcc  14040
agaaggtcga tagaaagcgt gagaaacagc gtacagacga tttagagatg tagaggtact  14100
tttatgccga gaaaactttt tgcgtgtgac agtccttaaa atatacttag agcgtaagcg  14160
aaagtagtag cgacagctat taactttcgg ttgcaaagct ctaggatttt taatggacgc  14220
agcgcatcac acgcaaaaag gaaattggaa taaatgcgaa atttgagatg ttaattaaag  14280
acctttttga ggtctttttt tcttagattt ttggggttat ttaggggaga aaacataggg  14340
gggtactacg acctcccccc taggtgtcca ttgtccattg tccaaacaaa taaataaata  14400
ttgggttttt aatgttaaaa ggttgttttt tatgttaaag tgaaaaaaac agatgttggg  14460
aggtacagtg atagttgtag atagaaaaga agagaaaaaa gttgctgtta ctttaagact  14520
tacaacagaa gaaaatgaga tattaaatag aatcaaagaa aaatataata ttagcaaatc  14580
agatgcaacc ggtattctaa taaaaaaata tgcaaaggag gaatacggtg cattttaaac  14640
aaaaaaagat agacagcact ggcatgctgc ctatctatga ctaaattttg ttaagtgtat  14700
tagcaccgtt attatatcat gagcgaaaat gtaataaaag aaactgaaaa caagaaaaat  14760
tcaagaggac gtaattggac atttgtttta tatccagaat cagcaaaagc cgagtggtta  14820
gagtatttaa aagagttaca cattcaattt gtagtgtctc cattacatga tagggatact  14880
gatacagaag gtaggatgaa aaaagagcat tatcatattc tagtgatgta tgagggtaat  14940
aaatcttatg aacagataaa aataattaac agaagaattg aatgcgacta ttccgcagat  15000
tgcaggaagt gtgaaaggtc ttgtgagata tatgcttcac atggacgatc ctaataaatt  15060
taaatatcaa aaagaagata tgatagttta tggcggtgta gatgttgatg aattattaaa  15120
gaaaacaaca acagatagat ataaattaat taaagaaatg attgagttta ttgatgaaca  15180
aggaatcgta gaatttaaga gtttaatgga ttatgcaatg aagtttaaat ttgatgattg  15240
gttcccgctt ttatgtgata actcggcgta tgttattcaa gaatatataa aatcaaatcg  15300
gtataaatct gaccgataga ttttgaattt aggtgtcaca agacactctt ttttcgcacc  15360
agcgaaaact ggtttaagcc gactgcgcaa aagacataat cgattcacaa aaaataggca  15420
cacgaaaaac aagttaaggg atgcagttta tgcatccctt aacttactta ttaaataatt  15480
tatagctatt gaaaagagat aagaattgtt caaagctaat attgtttaaa tcgtcaattc  15540
ctgcatgttt taaggaattg ttaaattgat tttttgtaaa tattttcttg tattctttgt  15600
taacgatgcg atggcggagt tccaggggat acatcaggag atggaaaggc agagagagcg  15660
cgaacgtctg gcggaaaaac agcgtcagca ggagaaagaa cgacagcgac tcgccgaaca  15720
gatacgacag aagccggata aaggctggtc attctcacga taggcaggat tttgtatgag  15780
cgacgaaatt aaacaaattg ccgcccttat cgggcatcat caggcgctgg aaaagcgtgt  15840
tacttctctg acagaacagt ttcaggccgc ctcatcacaa ttacagcagc aaagtgaaac  15900
gctgagcagg gtcattcgtg agctggacag cgcgtccggt aatatgactg acaccgtcag  15960
gaaatcggtg agttccgcgc tcactcaggt tgagaaagaa ctgaaacaag ccggattagc  16020
acagcagaaa ccggcgacag aagcgctgaa tcaggctgcc gatacggcga aagcgatgat  16080
ccatgaaatg cgtcgtgaga tgtcacgcta tacgtggaaa tccgcgattt atcttgtact  16140
gacgatattc ttcgtcctgg cttcctgcgt gacggcattt acgtggttta tgaatgacgg  16200
gtatagccag attgctgaaa tgcagaggat ggaagcggtc tggcaaaaga aagccccgct  16260
ggctgacata tcgcgctgtg acggaaagcc ctgcgttaag gtggacactc gcactacgta  16320
```

-continued tggtgataaa gagaatacct ggatgattat taagaaataa catcatagac acagaagcct 16380
gtgcgtcgat ctccggcgga gaaagcatta attaaacgtg tcggggggat ctgataaccc 16440
cagcaaataa aggacattaa ggatatgggg tctgaaggcc aatagaacga aaacgtacgt 16500
tagtgaagta actgtctgat atatcgaaac ataatgtaca ttggaaaacg ccatcaaaac 16560
ggtgtctttt taatcgaaaa ttggcactta acggactttc ttgtctacta atcgatacaa 16620
attccccgta ggcgctaggg acctctttag ctccttggaa gctgtcagta gtatacctaa 16680
taatttatct acattccctt tagtaacgtg taactttcca aatttacaaa agcgactcat 16740
agaattattt cctcccgtta aataatagat aactattaaa aatagacaat acttgctcat 16800
aagtaacggt acttaaattg tttactttgg cgtgtttcat tgcttgatga aactgatttt 16860
tagtaaacag ttgacgatat tctcgattga cccattttga aacaaagtac gtatatagct 16920
tccaatattt atctggaaca tctgtggtat ggcgggtaag ttttattaag acactgttta 16980
cttttggttt aggatgaaag cattccgctg gcagcttaag caattgctga atcgagactt 17040
gagtgtgcaa gagcaaccct agtgttcggt gaatatccaa ggtacgcttg tagaatcctt 17100
cttcaacaat cagatagatg tcagacgcat ggctttcaaa aaccactttt ttaataattt 17160
gtgtgcttaa atggtaagga atattcccaa caattttata cctctgtttg ttagggaatt 17220
gaaactgtag aatatcttgg tgaattaaag tgacacgaat gttcagtttt aatttttctg 17280
acgataagtt gaatagatga ctgtctaatt caatagacgt tacctgttta cttattttag 17340
ccagtttcgt cgttaaatgc cctttacctg ttccaatttc gtaaacggta tcggtttctt 17400
ttaaattcaa ttgttttatt atttggttga gtactttttc actcgttaaa aagttttgag 17460
aatattttat atttttgttc atgtaatcac tccttcttaa ttacaaattt ttagcattta 17520
atttaacttc aattcctatt atacaaaatt ttaagatact gcactatcaa cacactctta 17580
agtttgcttc taagtcttat ttccataact tcttttacgt ttccgccatt ctttgctgtt 17640
tcgattttta tgatatggtg caagtcagca cgaacacgaa ccgtcttatc tcccattata 17700
tctttttttg cactgattgg tgtatcattt cgtttttctt tttgtgcgcc taaatttccc 17760
acaatcactc acttctttct atttcttctt attcttattt tatcatcaac aatcacaaat 17820
cacttgtgat ttgtgataag tgatttgtga ttaatatata aaagccctct ttaaagggct 17880
tttatgttta ttttgagaaa gatataaaat caatatatcc cttttctccg atttttacaa 17940
cggcattgta ggactttcta tctttcgttt tgattccttt taccagggtt tcttttccct 18000
ctagtaattc ttttacattt gttttggtga gttttttctt tctaaaatgt tcagctaaag 18060
taaacttaca ttcaggataa tttgaacaac cataaaacga ttttttttaat acaatattgt 18120 tgccacactt aggacatttt cctacaatac tttttttctgc ttcttttttct ttctgttcct 18180 ggtaatcaga aaaatttagt ttttctatat cgttaggtac agcttccagt aaatgaacaa 18240
tgaatttttt gatattcgta ataaagttct cttgattgcc ttctctttta ccgatttttt 18300
ttaaatacgt ttcccattta gccgtcattt cagcactcgt taaaaggtgc tgacttt 18357

<210> SEQ ID NO 4
<211> LENGTH: 6418
<212> TYPE: DNA
<213> ORGANISM: Artificial Sequence
<220> FEATURE:
<223> OTHER INFORMATION: Plasmid

<400> SEQUENCE: 4
cgaacgctgc ggccgaactc ggcttcaccg aacgggcctg gttcacgatg gtcacaggtc 60
tcggcgcggc tgttgatcca gaccgatcgc ttactcaagc agctgacctt gacggatctg 120
gccaagttca cccaggcgtg tgacgaccgc ggcgcccgga ccggcaagcg accaggtcgc 180
aggcggctgt gagccgaaga gaaagtttga agtcagacaa ggcgaacgac ggcgggccag 240
gtcatttgta attcgagacc tgcttggccg aacgcgcgct acgaacctca taaacagcaa 300
taggtagtct tgccgagggt gggcaatgag gctcttcaga attgagggtg tagtttcggt 360
ctgaatccgc cggattccag gagcgagcgg gctatgtagt tggtgaggtt ccggaacccg 420
agggctgagc cgcggaggtg ttccagtctc ccgttaattg cttctgtggg gccgttcgat 480
gttccgggcc gatcgaagta cgccagcacg tcttctgccc gtcgtttgag ggtccgcccc 540
agcgtcttga gctcggtgag agcggccggg acgcctgtgc tgatggaatt gaccactgcc 600
tgcatgagct tctttccttg gatgcggtcc tgctcccggt acgcggcaat catgcgctga 660
tagatgcccc agctggcttc gacctcgacg tgcgcatcgg tggcgaacaa gtcccgaagg 720
cgttggcgtt gtttgtcggt gagcaggtca gcacccgtgt gcagcgtccg cctcgctttg 780
tagagaggat cgccggcccg tccacgatgc ccgcacgttg cctgctgaac gcgtcgcctg 840
cagacatcga gtgcatcgcc tgccaagcgg atgacgtgga agggatccat gaccggaaca 900
gcctcgggaa gctcttcggc agcggcgctt ttgaagccgg agaatccgtc catggccacg 960
acttccaccc cttcccgcca cgcttcaggg cgttcgttca gccacgtggc gaagacctgc 1020
tttgagcggc cctcgaccat gtccagcagc cgggaagggc ccgtgccgtc acggatcggt 1080
gtcagatcga tgatgacggt gacgtacttg tccccgcggc gggtgtgccg ccaaacatgc 1140
tcatcaacac caatgacctt cactccatcg aagcggtgcg ggtcatcgat caatacgcgc 1200
cggccctcgg ccagaacggc gttgttcgcg gtattccacg acacgcccag gccctcggca 1260
acccgggcca ccgtcagatg ctgacagacg atgccttcca atgcccagcg cagtccacgg 1320
cgggaaagct tcgctcttgg ttcagcagcc ttcgaggtct cctgccgcca cacataaccg 1380
cacccggtgc agcggtaacg tcggagcctc accagcaata tcgtgggccg ccaaccgaag 1440
ggttcatggc ccagccgccg ggtcacagta tcccgcggga tgccctcgca cccacatctg 1500
gaacaccact catcagcatc caccacacgg caggtaatga cagcacgatc agggtacaga 1560
cactgcccag tggcttccag gccgagctca tcgaggcgac agaatgtggt caggtcaggg 1620
cgctggagag tagcgttgga catgagggcc ttgcggtaga aaattcaaga tctagacaat 1680
ctgattctct cccgaggccc tcaccttgtc tgaatcacgc cgctagagct tgggctgcag 1740
gtcgacggat ccggtgcggc ttgctggagc gatcctgcat cccaaactca ccctcttccc 1800
ggtagcggcc tgcccatttc cgggcagtga tcggggagac catgaacatc tttgcggcga 1860
tcgtggccgg atagccgtct tcgacaatca gccgagctaa ccggagacgg gcacgaggag 1920
tgagaagagc gttcggatgg gtcatcaatt ggcctccgcc gcggtcttcg taagcgcgcg 1980
tctggtgaga agcatgatga cgagagcgat cgctgtcagc accgaagcga cccaaaccgg 2040
cgcgagcagc cccagcccgg tcgcgagccc gagcgcacca agcacgggcc ccgctgcagc 2100
tccgatattc aatgctgcgg ttgcgtacga accgcccatc gttggcgcac ccgatgctgc 2160
atacagcaca cgcgtgatca gagtactgcc gacgccgaac gacaggaatc cctgaacgag 2220
gacgaggacg ataagcgcaa cgggatgaga tgcgaccact gccaacacga tccagcctgt 2280
cagcaatagc ggtccgccga ctgcgagcac gaggccaggt cgttgatctg atagtcgtcc 2340
tgcgatcgtg acgccaagga acgatccgat gccgaacatc accagcgcga cggacaccca 2400
cgcttcggcc aagcccgcgg tctcggtcac gatgggtgcc aggaaggtga atgccgcaaa 2460

-continued ggtccctccg ttgatcagcg ctccgagtgc catggccagg atgagccgcg gcgtcgccaa 2520
ctggctgagc tcgacacgga gccttggtga ggtcgcgcta gtctcgctcc gaccaacatt 2580
gttcgtgacg ccacgaatga ctccaacggc cgcgggaata cagaggatgg cgatcgccca 2640
gaacgtcgtt cgccagccca gcgctgtgcc gagcagtgcc ccggcgggga cgcccacgac 2700
ggttgcgatc gtcgtgccgg agagcaggat cgacagtgca cgccccttct ggttcgctgg 2760
cacgagggta gtggccgtgc tcagtgctac ggcgaggaat cctgcgtttg cgagagcgct 2820
gagcacccgg gtgatgagca ggagagagaa cactggtgtc atcgctccga tgacgtggct 2880
tcccgcgaac acgagaaggc aaacgatcaa tgtgagccgc ggtggccaac ggcgagcgaa 2940
tgccgccatc actggcgcgc cgacgaccat accgactgcg aatgcggagg tcagcaggcc 3000
cgcagtgccg accgagacgt caagttcggt cgcgatcgcg gggagcaatc ccgcgagcat 3060
gaattctgaa gtgcccatga cgaagaccgc cagggcaagc atgtagaggg caaaaggcat 3120
cgagtactcc gaggtgtgag atcaagaaat ggttcttctt gtcaccacgg ccagcgcccc 3180
gggtacgcca gacatacgcc cacacagatc gtgggcgtcg taactagtgg ttcaaggggc 3240
tggcggtgtg accgacaacc cctgacctgt ctgattcggg actcgacatg ccccaaactc 3300
taacatgcct tcaaggcgga atcaagcggt ggatgcgcca cgcttgaata gttcgttaag 3360
tatttcacgt ggggttgcgc cgccgaggat ttgtcggggt gtttcgttga gctcattttg 3420
cacccacgcg acatgttcgg gtgtgacggt ggcaaagtcg gtgccctttt tgtagaacct 3480
gcgcctgatc tcgccgttgg tgttctcgtt ggttggtctc tgccacggtg agtgcggttc 3540
acagaaaaac acctggcagc cgtctttaat ctggacttgt gctgtgacag ccatttctgc 3600
gccttggtcc catgtgatgg tctttagctg ctcggtgttg aggtctttga ccatgtcctg 3660
caggtcgacc tgcagcccaa gctctagccc tcggcgctgc atgcagttgc gcccactaca 3720
ccctcaattc tgaagagcca tggtaccgga attcactggc cgtcgtttta caacgtcgtg 3780
actgggaaaa ccctggcgtt acccaactta atcgccttgc agcacatccc cctttcgcca 3840
gctggcgtaa tagcgaagag gcccgcaccg atcgcccttc ccaacagttg cgcagcctga 3900
atggcgaatg gcgcctgatg cggtattttc tccttacgca tctgtgcggt atttcacacc 3960
gcatatggtg cactctcagt acaatctgct ctgatgccgc atagttaagc cagccccgac 4020
acccgccaac acccgctgac gcgccctgac gggcttgtct gctcccggca tccgcttaca 4080
gacaagctgt gaccgtctcc gggagctgca tgtgtcagag gttttcaccg tcatcaccga 4140
aacgcgcgag acgaaagggc ctcgtgatac gcctattttt ataggttaat gtcatgataa 4200
taatggtttc ttagacgtca ggtggcactt ttcggggaaa tgtgcgcgga acccctattt 4260
gtttattttt ctaaatacat tcaaatatgt atccgctcat gagacaataa ccctgataaa 4320
tgcttcaata atattgaaaa aggaagagta tgagtattca acatttccgt gtcgccctta 4380
ttcccttttt tgcggcattt tgccttcctg tttttgctca cccagaaacg ctggtgaaag 4440
taaaagatgc tgaagatcag ttgggtgcac gagtgggtta catcgaactg gatctcaaca 4500
gcggtaagat ccttgagagt tttcgccccg aagaacgttt tccaatgatg agcactttta 4560
aagttctgct atgtggcgcg gtattatccc gtattgacgc cgggcaagag caactcggtc 4620
gccgcataca ctattctcag aatgacttgg ttgagtactc accagtcaca gaaaagcatc 4680
ttacggatgg catgacagta agagaattat gcagtgctgc cataaccatg agtgataaca 4740
ctgcggccaa cttacttctg acaacgatcg gaggaccgaa ggagctaacc gcttttttgc 4800
acaacatggg ggatcatgta actcgccttg atcgttggga accggagctg aatgaagcca 4860

```
taccaaacga cgagcgtgac accacgatgc ctgtagcaat ggcaacaacg ttgcgcaaac   4920

tattaactgg cgaactactt actctagctt cccggcaaca attaatagac tggatggagg   4980

cggataaagt tgcaggacca cttctgcgct cggcccttcc ggctggctgg tttattgctg   5040

ataaatctgg agccggtgag cgtgggtctc gcggtatcat tgcagcactg gggccagatg   5100

gtaagccctc ccgtatcgta gttatctaca cgacggggag tcaggcaact atggatgaac   5160

gaaatagaca gatcgctgag ataggtgcct cactgattaa gcattggtaa ctgtcagacc   5220

aagtttactc atatatactt tagattgatt taaaacttca tttttaattt aaaaggatct   5280

aggtgaagat cctttttgat aatctcatga ccaaaatccc ttaacgtgag ttttcgttcc   5340

actgagcgtc agaccccgta gaaaagatca aaggatcttc ttgagatcct ttttttctgc   5400

gcgtaatctg ctgcttgcaa acaaaaaaac caccgctacc agcggtggtt tgtttgccgg   5460

atcaagagct accaactctt tttccgaagg taactggctt cagcagagcg cagataccaa   5520

atactgtcct tctagtgtag ccgtagttag gccaccactt caagaactct gtagcaccgc   5580

ctacatacct cgctctgcta atcctgttac cagtggctgc tgccagtggc gataagtcgt   5640

gtcttaccgg gttggactca agacgatagt taccggataa ggcgcagcgg tcgggctgaa   5700

cggggggttc gtgcacacag cccagcttgg agcgaacgac ctacaccgaa ctgagatacc   5760

tacagcgtga gctatgagaa agcgccacgc ttcccgaagg gagaaaggcg gacaggtatc   5820

cggtaagcgg cagggtcgga acaggagagc gcacgaggga gcttccaggg ggaaacgcct   5880

ggtatcttta tagtcctgtc gggtttcgcc acctctgact tgagcgtcga tttttgtgat   5940

gctcgtcagg ggggcggagc ctatggaaaa acgccagcaa cgcggccttt ttacggttcc   6000

tggccttttg ctggcctttt gctcacatgt tctttcctgc gttatcccct gattctgtgg   6060

ataaccgtat taccgccttt gagtgagctg ataccgctcg ccgcagccga acgaccgagc   6120

gcagcgagtc agtgagcgag gaagcggaag agcgcccaat acgcaaaccg cctctccccg   6180

cgcgttggcc gattcattaa tgcagctggc acgacaggtt tcccgactgg aaagcgggca   6240

gtgagcgcaa cgcaattaat gtgagttagc tcactcatta ggcaccccag gctttacact   6300

ttatgcttcc ggctcgtatg ttgtgtggaa ttgtgagcgg ataacaattt cacacaggaa   6360

acagctatga ccatgattac gccaagcttg gctgcaggt cgactctaga ggatcccc      6418
```

<210> SEQ ID NO 5
<211> LENGTH: 30
<212> TYPE: DNA
<213> ORGANISM: Artificial Sequence
<220> FEATURE:
<223> OTHER INFORMATION: Primer

<400> SEQUENCE: 5

```
ataaaagaat tcgactcctg tgaaatgatc                                     30
```

<210> SEQ ID NO 6
<211> LENGTH: 32
<212> TYPE: DNA
<213> ORGANISM: Artificial Sequence
<220> FEATURE:
<223> OTHER INFORMATION: Primer

<400> SEQUENCE: 6

```
aaaaaactcg accggatgta cttcagaaaa ga                                  32
```

<210> SEQ ID NO 7
<211> LENGTH: 32

<212> TYPE: DNA
<213> ORGANISM: Artificial Sequence
<220> FEATURE:
<223> OTHER INFORMATION: Primer

<400> SEQUENCE: 7
aaaaaagcgg ccgcatcacg ccgctagagc tt 32

<210> SEQ ID NO 8
<211> LENGTH: 32
<212> TYPE: DNA
<213> ORGANISM: Artificial Sequence
<220> FEATURE:
<223> OTHER INFORMATION: Primer

<400> SEQUENCE: 8
aaaaaactcg agtcagagaa ggtgagggcc tc 32

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
gaagcgtttg atagttaagt 20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ggtactaaaa caattcatcc 20

<210> SEQ ID NO 11
<211> LENGTH: 34
<212> TYPE: DNA
<213> ORGANISM: Artificial Sequence
<220> FEATURE:
<223> OTHER INFORMATION: Primer

<400> SEQUENCE: 11
ataaaagcgg ccgcgaaaca gctatgacca tgat 34

<210> SEQ ID NO 12
<211> LENGTH: 32
<212> TYPE: DNA
<213> ORGANISM: Artificial Sequence
<220> FEATURE:
<223> OTHER INFORMATION: Primer

<400> SEQUENCE: 12
aaaaaactcg agttattatt tccctcctcg ac 32

<210> SEQ ID NO 13
<211> LENGTH: 32
<212> TYPE: DNA
<213> ORGANISM: Artificial Sequence
<220> FEATURE:
<223> OTHER INFORMATION: Primer

<400> SEQUENCE: 13
aaaaaactcg agatcacgcc gctagagctt gg 32

-continued

```
<210> SEQ ID NO 14
<211> LENGTH: 34
<212> TYPE: DNA
<213> ORGANISM: Artificial Sequence
<220> FEATURE:
<223> OTHER INFORMATION: Primer

<400> SEQUENCE: 14

aaaaaagcgg ccgctcagac aaggtgaggg cctc                              34


<210> SEQ ID NO 15
<211> LENGTH: 19
<212> TYPE: DNA
<213> ORGANISM: Artificial Sequence
<220> FEATURE:
<223> OTHER INFORMATION: Primer

<400> SEQUENCE: 15

agagtactgc cgacgccga                                               19


<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16

actgtcgatc ctgctctccg                                              20


<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17

ggatttgtcg gggtgtttcg                                              20


<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18

cggccccaca gaagcaatta                                              20
```